(12) United States Patent
Kurukchi et al.

(10) Patent No.: US 8,815,050 B2
(45) Date of Patent: Aug. 26, 2014

(54) PROCESSES AND SYSTEMS FOR DRYING LIQUID BROMINE

(75) Inventors: Sabah A. Kurukchi, Houston, TX (US); Yijun Liu, Houston, TX (US); Anand Moodley, Houston, TX (US)

(73) Assignee: Marathon GTF Technology, Ltd., Houston, TX (US)

( * ) Notice: Subject to any disclaimer, the term of this patent is extended or adjusted under 35 U.S.C. 154(b) by 371 days.

(21) Appl. No.: 13/053,540

(22) Filed: Mar. 22, 2011

(65) Prior Publication Data

US 2012/0245399 A1    Sep. 27, 2012

(51) Int. Cl.
| | | |
|---|---|---|
| *B01D 1/00* | (2006.01) | |
| *B01D 12/00* | (2006.01) | |
| *F26B 7/00* | (2006.01) | |
| *F26B 3/00* | (2006.01) | |
| *C07C 17/10* | (2006.01) | |
| *C07C 1/30* | (2006.01) | |
| *C01B 7/09* | (2006.01) | |

(52) U.S. Cl.
CPC ............... *C01B 7/096* (2013.01); *C07C 17/10* (2013.01); *C07C 1/30* (2013.01); *C07C 2529/89* (2013.01)
USPC ............. 159/47.1; 34/443; 34/468; 159/47.3; 210/770; 210/774; 570/255; 585/641

(58) Field of Classification Search
CPC ............... B01D 1/00; C02F 1/02; F26B 3/00; F26B 7/00; C01B 7/096; C07C 1/30; C07C 17/10; C07C 19/075; C07C 2529/89; C07C 11/00

USPC ............. 34/202, 329, 337, 407, 443, 468; 159/47.1, 47.3; 210/770, 774, 806, 210/808; 203/12, 21, 25, 47, 71, 99; 570/181, 252, 255, 262; 585/641, 800, 585/802; 423/500–507

See application file for complete search history.

(56) References Cited

U.S. PATENT DOCUMENTS

| | | |
|---|---|---|
| 2,168,260 A | 8/1939 | Heisel et al. |
| 2,246,082 A | 6/1941 | Vaughan et al. |

(Continued)

FOREIGN PATENT DOCUMENTS

| | | |
|---|---|---|
| CA | 1099656 | 4/1981 |
| CA | 1101441 | 5/1981 |

(Continued)

OTHER PUBLICATIONS

U.S. Office Communication from U.S. Appl. No. 10/365,346 dated Jun. 12, 2006.

(Continued)

*Primary Examiner* — Joseph Drodge
(74) *Attorney, Agent, or Firm* — Jack E. Ebel; Corey S. Tumey; Rodney F. Brown

(57) ABSTRACT

Processes and systems for drying liquid bromine utilizing two fractionators to produce a substantially dry liquid bromine stream and a substantially bromine-free water stream. Wet bromine liquid may be conveyed to a first fractionator wherein a substantially dry bromine liquid is produced, while a vapor stream from the first fractionator may be condensed into a first liquid phase comprising bromine saturated with water and a second liquid phase comprising water saturated with bromine. The water saturated with bromine may be conveyed to a second fractionator to produce at least substantially bromine-free water.

16 Claims, 4 Drawing Sheets

(56) References Cited

U.S. PATENT DOCUMENTS

| | | |
|---|---|---|
| 2,320,257 A | 5/1943 | Beekhuis |
| 2,488,083 A | 11/1949 | Gorin et al. |
| 2,536,457 A | 1/1951 | Mugdan |
| 2,666,024 A | 1/1954 | Low et al. |
| 2,677,598 A | 5/1954 | Crummett et al. |
| 2,809,930 A | 10/1957 | Miller |
| 2,941,014 A | 6/1960 | Rothweiler et al. |
| 3,076,784 A | 2/1963 | Schulte-Huemann et al. |
| 3,172,915 A | 3/1965 | Borkowski et al. |
| 3,181,934 A | 5/1965 | Davis |
| 3,233,972 A * | 2/1966 | Walker et al. ............. 203/28 |
| 3,240,564 A | 3/1966 | Uffelmann et al. |
| 3,246,043 A | 4/1966 | Rosset et al. |
| 3,254,023 A | 5/1966 | Miale et al. |
| 3,273,964 A | 9/1966 | Rosset |
| 3,291,708 A | 12/1966 | Juda |
| 3,294,846 A | 12/1966 | Livak et al. |
| 3,310,380 A | 3/1967 | Lester |
| 3,314,762 A | 4/1967 | Hahn |
| 3,346,340 A | 10/1967 | Louvar et al. |
| 3,353,916 A | 11/1967 | Lester |
| 3,353,919 A | 11/1967 | Stockman |
| 3,379,506 A | 4/1968 | Massonne et al. |
| 3,468,968 A | 9/1969 | Baker et al. |
| 3,496,242 A | 2/1970 | Berkowitz et al. |
| 3,562,321 A | 2/1971 | Borkowski et al. |
| 3,598,876 A | 8/1971 | Bloch |
| 3,615,265 A | 10/1971 | Gartner |
| 3,642,447 A * | 2/1972 | Hahn et al. ............. 423/503 |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,816,599 A | 6/1974 | Kafes |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,927,111 A | 12/1975 | Robinson |
| 3,928,483 A | 12/1975 | Chang et al. |
| 3,959,450 A * | 5/1976 | Calloue et al. ............. 423/507 |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,819 A | 9/1977 | Schmerling |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Given et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A | 3/1979 | Kaeding et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A | 3/1980 | Coker et al. |
| 4,194,990 A | 3/1980 | Pieters et al. |
| 4,197,420 A | 4/1980 | Ferraris et al. |
| 4,219,604 A | 8/1980 | Kakimi et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,356,159 A | 10/1982 | Norval et al. |
| 4,371,716 A | 2/1983 | Paxson et al. |
| 4,373,109 A | 2/1983 | Olah |
| 4,376,019 A | 3/1983 | Gamlen et al. |
| 4,379,734 A * | 4/1983 | Franzen ............. 159/17.1 |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |

(56) References Cited

U.S. PATENT DOCUMENTS

| | | |
|---|---|---|
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,626,607 A | 12/1986 | Jacquinot et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,725,425 A † | 2/1988 | Lesher |
| 4,735,747 A | 4/1988 | Ollivier et al. |
| 4,737,594 A | 4/1988 | Olah |
| 4,748,013 A | 5/1988 | Saito et al. |
| 4,762,596 A | 8/1988 | Huang et al. |
| 4,769,504 A | 9/1988 | Noceti et al. |
| 4,774,216 A | 9/1988 | Kolts et al. |
| 4,775,462 A | 10/1988 | Imai et al. |
| 4,777,321 A | 10/1988 | Harandi et al. |
| 4,781,733 A | 11/1988 | Babcock et al. |
| 4,783,566 A | 11/1988 | Kocal et al. |
| 4,788,369 A | 11/1988 | Marsh et al. |
| 4,788,377 A | 11/1988 | Chang et al. |
| 4,792,642 A | 12/1988 | Rule et al. |
| 4,795,732 A | 1/1989 | Barri |
| 4,795,737 A | 1/1989 | Rule et al. |
| 4,795,843 A | 1/1989 | Imai et al. |
| 4,795,848 A | 1/1989 | Teller et al. |
| 4,804,797 A | 2/1989 | Minet et al. |
| 4,804,800 A | 2/1989 | Bortinger et al. |
| 4,808,763 A | 2/1989 | Shum |
| 4,814,527 A | 3/1989 | Diesen |
| 4,814,532 A | 3/1989 | Yoshida et al. |
| 4,814,535 A | 3/1989 | Yurchak |
| 4,814,536 A | 3/1989 | Yurchak |
| 4,849,562 A | 7/1989 | Buhs et al. |
| 4,849,573 A | 7/1989 | Kaefing |
| 4,851,602 A | 7/1989 | Harandi et al. |
| 4,851,606 A | 7/1989 | Ragonese et al. |
| 4,886,925 A | 12/1989 | Harandi |
| 4,886,932 A | 12/1989 | Leyshon |
| 4,891,463 A | 1/1990 | Chu |
| 4,895,995 A | 1/1990 | James, Jr. et al. |
| 4,899,000 A | 2/1990 | Stauffer |
| 4,899,001 A | 2/1990 | Kalnes et al. |
| 4,899,002 A | 2/1990 | Harandi et al. |
| 4,902,842 A | 2/1990 | Kalnes et al. |
| 4,925,995 A | 5/1990 | Robschlager |
| 4,929,781 A | 5/1990 | James, Jr. et al. |
| 4,939,310 A | 7/1990 | Wade |
| 4,939,311 A | 7/1990 | Washecheck et al. |
| 4,939,314 A | 7/1990 | Harandi et al. |
| 4,945,175 A | 7/1990 | Hobbs et al. |
| 4,950,811 A | 8/1990 | Doussain et al. |
| 4,950,822 A | 8/1990 | Dileo et al. |
| 4,956,521 A | 9/1990 | Volles |
| 4,962,252 A | 10/1990 | Wade |
| 4,973,776 A | 11/1990 | Allenger et al. |
| 4,973,786 A | 11/1990 | Karra |
| 4,982,024 A | 1/1991 | Lin et al. |
| 4,982,041 A | 1/1991 | Campbell |
| 4,988,660 A | 1/1991 | Campbell |
| 4,990,696 A | 2/1991 | Stauffer |
| 4,990,711 A | 2/1991 | Chen et al. |
| 5,001,293 A | 3/1991 | Nubel et al. |
| 5,004,847 A | 4/1991 | Beaver et al. |
| 5,013,424 A | 5/1991 | James, Jr. et al. |
| 5,013,793 A | 5/1991 | Wang et al. |
| 5,019,652 A | 5/1991 | Taylor et al. |
| 5,026,934 A | 6/1991 | Bains et al. |
| 5,026,937 A | 6/1991 | Bricker |
| 5,026,944 A | 6/1991 | Allenger et al. |
| 5,034,566 A | 7/1991 | Ishino et al. |
| 5,043,502 A | 8/1991 | Martindale et al. |
| 5,055,235 A | 10/1991 | Brackenridge et al. |
| 5,055,625 A | 10/1991 | Neidiffer et al. |
| 5,055,633 A | 10/1991 | Volles |
| 5,055,634 A | 10/1991 | Volles |
| 5,059,744 A | 10/1991 | Harandi et al. |
| 5,068,478 A | 11/1991 | Miller et al. |
| 5,071,449 A | 12/1991 | Sircar |
| 5,071,815 A | 12/1991 | Wallace et al. |
| 5,073,656 A | 12/1991 | Chafin et al. |
| 5,073,657 A | 12/1991 | Warren |
| 5,082,473 A | 1/1992 | Keefer |
| 5,082,816 A | 1/1992 | Teller et al. |
| 5,085,674 A | 2/1992 | Leavitt |
| 5,087,779 A | 2/1992 | Nubel et al. |
| 5,087,786 A | 2/1992 | Nubel et al. |
| 5,087,787 A | 2/1992 | Kimble et al. |
| 5,093,533 A | 3/1992 | Wilson |
| 5,093,542 A | 3/1992 | Gaffney |
| 5,096,469 A | 3/1992 | Keefer |
| 5,097,083 A | 3/1992 | Stauffer |
| 5,099,084 A | 3/1992 | Stauffer |
| 5,105,045 A | 4/1992 | Kimble et al. |
| 5,105,046 A | 4/1992 | Washecheck |
| 5,107,032 A | 4/1992 | Erb et al. |
| 5,107,051 A | 4/1992 | Pannell |
| 5,107,061 A | 4/1992 | Ou et al. |
| 5,108,579 A | 4/1992 | Casci |
| 5,118,899 A | 6/1992 | Kimble et al. |
| 5,120,332 A | 6/1992 | Wells |
| 5,132,343 A | 7/1992 | Zwecker et al. |
| 5,138,112 A | 8/1992 | Gosling et al. |
| 5,139,991 A | 8/1992 | Taylor et al. |
| 5,146,027 A | 9/1992 | Gaffney |
| 5,157,189 A | 10/1992 | Karra |
| 5,160,502 A | 11/1992 | Kimble et al. |
| 5,166,452 A | 11/1992 | Gradl et al. |
| 5,175,382 A | 12/1992 | Hebgen et al. |
| 5,178,748 A | 1/1993 | Casci et al. |
| 5,185,479 A | 2/1993 | Stauffer |
| 5,188,725 A | 2/1993 | Harandi |
| 5,191,142 A | 3/1993 | Marshall et al. |
| 5,194,244 A | 3/1993 | Brownscombe et al. |
| 5,202,506 A | 4/1993 | Kirchner et al. |
| 5,202,511 A | 4/1993 | Salinas, III et al. |
| 5,208,402 A | 5/1993 | Wilson |
| 5,210,357 A | 5/1993 | Kolts et al. |
| 5,215,648 A | 6/1993 | Zones et al. |
| 5,223,471 A | 6/1993 | Washecheck |
| 5,228,888 A | 7/1993 | Gmelin et al. |

(56) References Cited

U.S. PATENT DOCUMENTS

| | | |
|---|---|---|
| 5,233,113 A | 8/1993 | Periana et al. |
| 5,237,115 A | 8/1993 | Makovec et al. |
| 5,243,098 A | 9/1993 | Miller et al. |
| 5,243,114 A | 9/1993 | Johnson et al. |
| 5,245,109 A | 9/1993 | Kaminsky et al. |
| 5,254,772 A | 10/1993 | Dukat et al. |
| 5,254,790 A | 10/1993 | Thomas et al. |
| 5,264,635 A | 11/1993 | Le et al. |
| 5,268,518 A | 12/1993 | West et al. |
| 5,276,226 A | 1/1994 | Horvath et al. |
| 5,276,240 A | 1/1994 | Timmons et al. |
| 5,276,242 A | 1/1994 | Wu |
| 5,284,990 A | 2/1994 | Peterson et al. |
| 5,300,126 A | 4/1994 | Brown et al. |
| 5,306,855 A | 4/1994 | Periana et al. |
| 5,316,995 A | 5/1994 | Kaminsky et al. |
| 5,319,132 A | 6/1994 | Ozawa et al. |
| 5,334,777 A | 8/1994 | Miller et al. |
| 5,345,021 A | 9/1994 | Casci et al. |
| 5,354,916 A | 10/1994 | Horvath et al. |
| 5,354,931 A | 10/1994 | Jan et al. |
| 5,358,645 A | 10/1994 | Hong et al. |
| 5,366,949 A | 11/1994 | Schubert |
| 5,371,313 A | 12/1994 | Ostrowicki |
| 5,382,704 A | 1/1995 | Krespan et al. |
| 5,382,743 A | 1/1995 | Beech, Jr. et al. |
| 5,382,744 A | 1/1995 | Abbott et al. |
| 5,385,650 A * | 1/1995 | Howarth et al. .............. 205/619 |
| 5,385,718 A | 1/1995 | Casci et al. |
| 5,395,981 A | 3/1995 | Marker |
| 5,399,258 A | 3/1995 | Fletcher et al. |
| 5,401,890 A | 3/1995 | Parks |
| 5,401,894 A | 3/1995 | Brasier et al. |
| 5,406,017 A | 4/1995 | Withers, Jr. |
| 5,411,641 A | 5/1995 | Trainham, III et al. |
| 5,414,173 A | 5/1995 | Garces et al. |
| 5,430,210 A | 7/1995 | Grasselli et al. |
| 5,430,214 A | 7/1995 | Smith et al. |
| 5,430,219 A | 7/1995 | Sanfilippo et al. |
| 5,433,828 A | 7/1995 | van Velzen et al. |
| 5,436,378 A | 7/1995 | Masini et al. |
| 5,444,168 A | 8/1995 | Brown |
| 5,446,234 A | 8/1995 | Casci et al. |
| 5,453,557 A | 9/1995 | Harley et al. |
| 5,456,822 A | 10/1995 | Marcilly et al. |
| 5,457,255 A | 10/1995 | Kumata et al. |
| 5,464,799 A | 11/1995 | Casci et al. |
| 5,465,699 A | 11/1995 | Voigt |
| 5,470,377 A | 11/1995 | Whitlock |
| 5,480,629 A | 1/1996 | Thompson et al. |
| 5,486,627 A | 1/1996 | Quarderer, Jr. et al. |
| 5,489,719 A | 2/1996 | Le et al. |
| 5,489,727 A | 2/1996 | Randolph et al. |
| 5,500,297 A | 3/1996 | Thompson et al. |
| 5,510,525 A | 4/1996 | Sen et al. |
| 5,523,503 A | 6/1996 | Funk et al. |
| 5,525,230 A | 6/1996 | Wrigley et al. |
| 5,538,540 A | 7/1996 | Whitlock |
| 5,563,313 A | 10/1996 | Chung et al. |
| 5,565,092 A | 10/1996 | Pannell et al. |
| 5,565,616 A | 10/1996 | Li et al. |
| 5,571,762 A | 11/1996 | Clerici et al. |
| 5,571,885 A | 11/1996 | Chung et al. |
| 5,599,381 A | 2/1997 | Whitlock |
| 5,600,043 A | 2/1997 | Johnston et al. |
| 5,600,045 A | 2/1997 | Van Der Aalst et al. |
| 5,609,654 A | 3/1997 | Le et al. |
| 5,633,419 A | 5/1997 | Spencer et al. |
| 5,639,930 A | 6/1997 | Penick |
| 5,653,956 A | 8/1997 | Zones |
| 5,656,149 A | 8/1997 | Zones et al. |
| 5,661,097 A | 8/1997 | Spencer et al. |
| 5,663,465 A | 9/1997 | Clegg et al. |
| 5,663,474 A | 9/1997 | Pham et al. |
| 5,674,464 A | 10/1997 | Van Velzen et al. |
| 5,675,046 A | 10/1997 | Ohno et al. |
| 5,675,052 A | 10/1997 | Menon et al. |
| 5,679,134 A | 10/1997 | Brugerolle et al. |
| 5,679,879 A | 10/1997 | Mercier et al. |
| 5,684,213 A | 11/1997 | Nemphos et al. |
| 5,693,191 A | 12/1997 | Pividal et al. |
| 5,695,890 A | 12/1997 | Thompson et al. |
| 5,698,747 A | 12/1997 | Godwin et al. |
| 5,705,712 A | 1/1998 | Frey et al. |
| 5,705,728 A | 1/1998 | Viswanathan et al. |
| 5,705,729 A | 1/1998 | Huang |
| 5,708,246 A | 1/1998 | Camaioni et al. |
| 5,720,858 A | 2/1998 | Noceti et al. |
| 5,728,897 A | 3/1998 | Buysch et al. |
| 5,728,905 A | 3/1998 | Clegg et al. |
| 5,734,073 A | 3/1998 | Chambers et al. |
| 5,741,949 A | 4/1998 | Mack |
| 5,744,669 A | 4/1998 | Kalnes et al. |
| 5,750,801 A | 5/1998 | Buysch et al. |
| 5,770,175 A | 6/1998 | Zones |
| 5,776,871 A | 7/1998 | Cothran et al. |
| 5,780,703 A | 7/1998 | Chang et al. |
| 5,782,936 A | 7/1998 | Riley |
| 5,798,314 A | 8/1998 | Spencer et al. |
| 5,814,715 A | 9/1998 | Chen et al. |
| 5,817,904 A | 10/1998 | Vic et al. |
| 5,821,394 A | 10/1998 | Schoebrechts et al. |
| 5,847,224 A | 12/1998 | Koga et al. |
| 5,849,978 A | 12/1998 | Benazzi et al. |
| 5,866,735 A | 2/1999 | Cheung et al. |
| 5,882,614 A | 3/1999 | Taylor, Jr. et al. |
| 5,895,831 A | 4/1999 | Brasier et al. |
| 5,898,086 A | 4/1999 | Harris |
| 5,905,169 A | 5/1999 | Jacobson |
| 5,906,892 A | 5/1999 | Thompson et al. |
| 5,908,963 A | 6/1999 | Voss et al. |
| 5,928,488 A | 7/1999 | Newman |
| 5,952,538 A | 9/1999 | Vaughn et al. |
| 5,959,170 A | 9/1999 | Withers, Jr. et al. |
| 5,968,236 A | 10/1999 | Bassine |
| 5,969,195 A | 10/1999 | Stabel et al. |
| 5,977,402 A | 11/1999 | Sekiguchi et al. |
| 5,983,476 A | 11/1999 | Eshelman et al. |
| 5,986,158 A | 11/1999 | Van Broekhoven et al. |
| 5,994,604 A | 11/1999 | Reagen et al. |
| 5,998,679 A | 12/1999 | Miller |
| 5,998,686 A | 12/1999 | Clem et al. |
| 6,002,059 A | 12/1999 | Hellring et al. |
| 6,015,867 A | 1/2000 | Fushimi et al. |
| 6,018,088 A | 1/2000 | Olah |
| 6,022,929 A | 2/2000 | Chen et al. |
| 6,034,288 A | 3/2000 | Scott et al. |
| 6,056,804 A | 5/2000 | Keefer et al. |
| 6,068,679 A | 5/2000 | Zheng |
| 6,072,091 A | 6/2000 | Cosyns et al. |
| 6,087,294 A | 7/2000 | Klabunde et al. |
| 6,090,312 A | 7/2000 | Ziaka et al. |
| 6,093,306 A | 7/2000 | Hanrahan et al. |
| 6,096,932 A | 8/2000 | Subramanian |
| 6,096,933 A | 8/2000 | Cheung et al. |
| 6,103,215 A | 8/2000 | Zones et al. |
| 6,107,561 A | 8/2000 | Thompson et al. |
| 6,117,371 A | 9/2000 | Mack |
| 6,124,514 A | 9/2000 | Emmrich et al. |
| 6,127,588 A | 10/2000 | Kimble et al. |
| 6,130,260 A | 10/2000 | Hall et al. |
| 6,143,939 A | 11/2000 | Farcasiu et al. |
| 6,169,218 B1 | 1/2001 | Hearn et al. |
| 6,180,841 B1 | 1/2001 | Fatutto et al. |
| 6,187,871 B1 | 2/2001 | Thompson et al. |
| 6,187,983 B1 | 2/2001 | Sun |
| 6,203,712 B1 | 3/2001 | Bronner et al. |
| 6,207,864 B1 | 3/2001 | Henningsen et al. |
| 6,225,517 B1 | 5/2001 | Nascimento et al. |
| 6,248,218 B1 | 6/2001 | Linkous et al. |
| 6,265,505 B1 | 7/2001 | McConville et al. |
| 6,281,405 B1 | 8/2001 | Davis et al. |
| 6,320,085 B1 | 11/2001 | Arvai et al. |
| 6,337,063 B1 | 1/2002 | Rouleau et al. |

(56) References Cited

U.S. PATENT DOCUMENTS

| | | |
|---|---|---|
| 6,342,200 B1 | 1/2002 | Rouleau et al. |
| 6,368,490 B1 | 4/2002 | Gestermann |
| 6,369,283 B1 | 4/2002 | Guram et al. |
| 6,372,949 B1 | 4/2002 | Brown et al. |
| 6,376,731 B1 | 4/2002 | Evans et al. |
| 6,380,328 B1 | 4/2002 | McConville et al. |
| 6,380,423 B2 | 4/2002 | Banning et al. |
| 6,380,444 B1 | 4/2002 | Bjerrum et al. |
| 6,395,945 B1 | 5/2002 | Randolph |
| 6,403,840 B1 | 6/2002 | Zhou et al. |
| 6,406,523 B1 | 6/2002 | Connor et al. |
| 6,423,211 B1 | 7/2002 | Randolph et al. |
| 6,426,441 B1 | 7/2002 | Randolph et al. |
| 6,426,442 B1 | 7/2002 | Ichikawa et al. |
| 6,452,058 B1 | 9/2002 | Schweizer et al. |
| 6,455,650 B1 | 9/2002 | Lipian et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,345 B2 | 10/2002 | Hintermann et al. |
| 6,472,572 B1 | 10/2002 | Zhou et al. |
| 6,475,463 B1 | 11/2002 | Elomari et al. |
| 6,475,464 B1 | 11/2002 | Rouleau et al. |
| 6,479,705 B2 | 11/2002 | Murata et al. |
| 6,482,997 B2 | 11/2002 | Petit-Clair et al. |
| 6,486,368 B1 | 11/2002 | Zhou et al. |
| 6,491,809 B1 | 12/2002 | Briot et al. |
| 6,495,484 B1 | 12/2002 | Holtcamp |
| 6,509,485 B2 | 1/2003 | Mul et al. |
| 6,511,526 B2 | 1/2003 | Jagger et al. |
| 6,514,319 B2 | 2/2003 | Keefer et al. |
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |
| 6,616,830 B2 | 9/2003 | Elomari |
| 6,620,757 B2 | 9/2003 | McConville et al. |
| 6,627,777 B2 | 9/2003 | Rossi et al. |
| 6,632,971 B2 | 10/2003 | Brown et al. |
| 6,635,793 B2 | 10/2003 | Mul et al. |
| 6,641,644 B2 | 11/2003 | Jagger et al. |
| 6,646,102 B2 | 11/2003 | Boriack et al. |
| 6,669,846 B2 | 12/2003 | Perriello |
| 6,672,572 B2 | 1/2004 | Werlen |
| 6,679,986 B1 | 1/2004 | Da Silva et al. |
| 6,680,415 B1 | 1/2004 | Gulotty, Jr. et al. |
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B1 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,870 B2 | 10/2005 | Yan et al. |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Santiago Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Santiago Fernandez et al. |
| 7,037,358 B2 | 5/2006 | Babicki et al. |
| 7,045,111 B1 † | 5/2006 | DeGroot |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,060,865 B2 | 6/2006 | Ding et al. |
| 7,064,238 B2 | 6/2006 | Waycuilis |
| 7,064,240 B2 | 6/2006 | Ohno et al. |
| 7,067,448 B1 | 6/2006 | Weitkamp et al. |
| 7,083,714 B2 | 8/2006 | Elomari |
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 | 12/2006 | Zhou et al. |
| 7,151,199 B2 | 12/2006 | Martens et al. |
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |

(56) References Cited

U.S. PATENT DOCUMENTS

| | | |
|---|---|---|
| 7,271,303 B1 | 9/2007 | Sechrist et al. |
| 7,273,957 B2 | 9/2007 | Bakshi et al. |
| 7,282,603 B2 | 10/2007 | Richards |
| 7,285,698 B2 | 10/2007 | Liu et al. |
| 7,304,193 B1 | 12/2007 | Frey et al. |
| 7,342,144 B2 | 3/2008 | Kaizik et al. |
| 7,348,295 B2 | 3/2008 | Zones et al. |
| 7,348,464 B2 | 3/2008 | Waycuilis |
| 7,357,904 B2 | 4/2008 | Zones et al. |
| 7,361,794 B2 | 4/2008 | Grosso |
| 7,365,102 B1 | 4/2008 | Weissman |
| 7,390,395 B2 | 6/2008 | Elomari |
| 7,560,607 B2 | 7/2009 | Waycuilis |
| 7,674,941 B2 | 3/2010 | Waycuilis et al. |
| 7,713,510 B2 * | 5/2010 | Harrod et al. ............. 423/502 |
| 7,880,041 B2 | 2/2011 | Waycuilis |
| 8,008,535 B2 | 8/2011 | Waycuilis |
| 8,173,851 B2 | 5/2012 | Waycuilis et al. |
| 8,198,495 B2 | 6/2012 | Waycuilis et al. |
| 8,232,441 B2 | 7/2012 | Waycuilis |
| 8,282,810 B2 | 10/2012 | Waycuilis |
| 8,367,884 B2 | 2/2013 | Waycuilis |
| 8,373,015 B2 | 2/2013 | Stark et al. |
| 8,415,517 B2 | 4/2013 | Gadewar et al. |
| 8,436,220 B2 | 5/2013 | Kurukchi et al. |
| 8,449,849 B2 | 5/2013 | Gadewar et al. |
| 8,642,822 B2 | 2/2014 | Brickey et al. |
| 2001/0051662 A1 | 12/2001 | Arcuri et al. |
| 2002/0102672 A1 | 8/2002 | Mizrahi |
| 2002/0193649 A1 | 12/2002 | O'Rear et al. |
| 2002/0198416 A1 | 12/2002 | Zhou et al. |
| 2003/0004380 A1 | 1/2003 | Grumann |
| 2003/0065239 A1 | 4/2003 | Zhu |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125589 A1 | 7/2003 | Grosso |
| 2003/0166973 A1 | 9/2003 | Zhou et al. |
| 2004/0006246 A1 | 1/2004 | Sherman et al. |
| 2004/0055955 A1 * | 3/2004 | Davis ............................ 210/652 |
| 2004/0062705 A1 | 4/2004 | Leduc |
| 2004/0152929 A1 | 8/2004 | Clarke |
| 2004/0158107 A1 | 8/2004 | Aoki |
| 2004/0158108 A1 | 8/2004 | Snoble |
| 2004/0171779 A1 | 9/2004 | Matyjaszewski et al. |
| 2004/0187684 A1 | 9/2004 | Elomari |
| 2004/0188271 A1 | 9/2004 | Ramachandraiah et al. |
| 2004/0188324 A1 | 9/2004 | Elomari |
| 2004/0220433 A1 | 11/2004 | Van Der Heide |
| 2005/0027084 A1 | 2/2005 | Clarke |
| 2005/0038310 A1 | 2/2005 | Lorkovic et al. |
| 2005/0042159 A1 | 2/2005 | Elomari |
| 2005/0047927 A1 | 3/2005 | Lee et al. |
| 2005/0148805 A1 | 7/2005 | Jones |
| 2005/0171393 A1 | 8/2005 | Lorkovic |
| 2005/0192468 A1 | 9/2005 | Sherman et al. |
| 2005/0215837 A1 | 9/2005 | Hoffpauir |
| 2005/0218041 A1 | 10/2005 | Yoshida et al. |
| 2005/0234276 A1 | 10/2005 | Waycuilis |
| 2005/0234277 A1 | 10/2005 | Waycuilis |
| 2005/0245771 A1 | 11/2005 | Fong et al. |
| 2005/0245772 A1 | 11/2005 | Fong |
| 2005/0245777 A1 | 11/2005 | Fong |
| 2005/0267224 A1 | 12/2005 | Herling |
| 2006/0025617 A1 | 2/2006 | Begley |
| 2006/0100469 A1 | 5/2006 | Waycuilis |
| 2006/0135823 A1 | 6/2006 | Jun |
| 2006/0138025 A1 | 6/2006 | Zones |
| 2006/0138026 A1 | 6/2006 | Chen |
| 2006/0149116 A1 | 7/2006 | Slaugh |
| 2006/0229228 A1 | 10/2006 | Komon et al. |
| 2006/0229475 A1 | 10/2006 | Weiss et al. |
| 2006/0270863 A1 | 11/2006 | Reiling |
| 2006/0288690 A1 | 12/2006 | Elomari |
| 2007/0004955 A1 | 1/2007 | Kay |
| 2007/0078285 A1 | 4/2007 | Dagle |
| 2007/0100189 A1 | 5/2007 | Stauffer |
| 2007/0129584 A1 | 6/2007 | Basset |
| 2007/0142680 A1 | 6/2007 | Ayoub |
| 2007/0148067 A1 | 6/2007 | Zones |
| 2007/0148086 A1 | 6/2007 | Zones |
| 2007/0149778 A1 | 6/2007 | Zones |
| 2007/0149789 A1 | 6/2007 | Zones |
| 2007/0149819 A1 | 6/2007 | Zones |
| 2007/0149824 A1 | 6/2007 | Zones |
| 2007/0149837 A1 | 6/2007 | Zones |
| 2007/0149838 A1 | 6/2007 | Chretien |
| 2007/0197801 A1 | 8/2007 | Bolk |
| 2007/0197847 A1 | 8/2007 | Liu |
| 2007/0213545 A1 | 9/2007 | Bolk |
| 2007/0238905 A1 | 10/2007 | Arredondo |
| 2007/0238909 A1 | 10/2007 | Gadewar et al. |
| 2007/0276168 A1 | 11/2007 | Garel |
| 2007/0284284 A1 | 12/2007 | Zones |
| 2008/0022717 A1 | 1/2008 | Yoshida et al. |
| 2008/0152555 A1 | 6/2008 | Wang et al. |
| 2008/0171898 A1 | 7/2008 | Waycuilis |
| 2008/0183022 A1 | 7/2008 | Waycuilis |
| 2008/0188697 A1 | 8/2008 | Lorkovic |
| 2008/0200740 A1 | 8/2008 | Waycuilis |
| 2008/0210596 A1 | 9/2008 | Litt et al. |
| 2008/0275279 A1 | 11/2008 | Podkolzin et al. |
| 2008/0275284 A1 | 11/2008 | Waycuilis |
| 2008/0314758 A1 | 12/2008 | Grosso et al. |
| 2009/0005620 A1 | 1/2009 | Waycuilis et al. |
| 2009/0163749 A1 | 6/2009 | Li et al. |
| 2009/0247796 A1 | 10/2009 | Waycuilis et al. |
| 2009/0270655 A1 | 10/2009 | Fong et al. |
| 2009/0306443 A1 | 12/2009 | Stark et al. |
| 2009/0308759 A1 | 12/2009 | Waycuilis |
| 2009/0312586 A1 | 12/2009 | Waycuilis et al. |
| 2009/0326292 A1 | 12/2009 | Waycuilis |
| 2010/0030005 A1 | 2/2010 | Sauer et al. |
| 2010/0087686 A1 | 4/2010 | Fong et al. |
| 2010/0096588 A1 | 4/2010 | Gadewar et al. |
| 2010/0099929 A1 | 4/2010 | Gadewar et al. |
| 2010/0099930 A1 | 4/2010 | Stoimenov et al. |
| 2010/0105972 A1 | 4/2010 | Lorkovic |
| 2010/0234637 A1 | 9/2010 | Fong et al. |
| 2010/0270167 A1 | 10/2010 | McFarland |
| 2011/0015458 A1 | 1/2011 | Waycuilis et al. |
| 2011/0071326 A1 | 3/2011 | Waycuilis |
| 2011/0198285 A1 * | 8/2011 | Wallace ........................ 210/638 |
| 2011/0218372 A1 | 9/2011 | Waycuilis et al. |
| 2011/0218374 A1 | 9/2011 | Waycuilis |
| 2012/0053381 A1 | 3/2012 | Evans et al. |
| 2012/0141356 A1 | 6/2012 | Brickey et al. |
| 2012/0313034 A1 | 12/2012 | Kurukchi et al. |
| 2013/0006024 A1 | 1/2013 | Kurukchi et al. |
| 2013/0046121 A1 | 2/2013 | Kurukchi et al. |
| 2013/0079564 A1 | 3/2013 | Waycuilis |
| 2013/0090504 A1 | 4/2013 | Roscoe et al. |
| 2013/0102820 A1 | 4/2013 | Waycuilis et al. |
| 2013/0102821 A1 | 4/2013 | Waycuilis et al. |
| 2013/0156681 A1 | 6/2013 | Kurukchi et al. |
| 2013/0158324 A1 | 6/2013 | Waycuilis et al. |
| 2013/0178675 A1 | 7/2013 | Kurukchi et al. |
| 2013/0217938 A1 | 8/2013 | Waycuilis et al. |
| 2014/0179963 A1 | 6/2014 | Waycuilis |

FOREIGN PATENT DOCUMENTS

| | | |
|---|---|---|
| CA | 1202610 | 4/1986 |
| CA | 2542857 | 5/2005 |
| CA | 2236126 | 8/2006 |
| CA | 2203115 | 9/2006 |
| CA | 2510093 | 12/2006 |
| CA | 2641348 A1 | 8/2007 |
| CA | 2684765 A1 | 11/2008 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |

(56) References Cited

FOREIGN PATENT DOCUMENTS

| | | |
|---|---|---|
| EP | 0526908 A2 | 2/1993 |
| EP | 0346612 B1 | 8/1993 |
| EP | 0560546 A1 | 9/1993 |
| EP | 0976705 A1 | 2/2000 |
| EP | 1186591 A2 | 3/2002 |
| EP | 1253126 A1 | 10/2002 |
| EP | 1312411 A2 | 5/2003 |
| EP | 1235769 B1 | 5/2004 |
| EP | 1435349 A2 | 7/2004 |
| EP | 1440939 A1 | 7/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 0/1912 |
| GB | 156122 | 3/1922 |
| GB | 294100 | 6/1929 |
| GB | 363009 | 12/1931 |
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 796085 | 6/1958 |
| GB | 883256 A | 11/1961 |
| GB | 930341 A | 7/1963 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| GB | 1172002 | 11/1969 |
| GB | 1212240 | 11/1970 |
| GB | 1233299 | 5/1971 |
| GB | 1253618 | 11/1971 |
| GB | 1263806 | 2/1972 |
| GB | 1446803 | 8/1976 |
| GB | 1542112 | 3/1979 |
| GB | 2095243 A | 9/1982 |
| GB | 2095245 A | 9/1982 |
| GB | 2095249 A | 9/1982 |
| GB | 2116546 A | 9/1982 |
| GB | 2120249 A | 11/1983 |
| GB | 2185754 A | 7/1987 |
| GB | 2191214 A | 12/1987 |
| SU | 694483 A1 | 10/1979 |
| WO | 83/00859 | 3/1983 |
| WO | 85/04863 | 11/1985 |
| WO | 85/04867 | 11/1985 |
| WO | 90/08120 | 7/1990 |
| WO | 90/08752 | 8/1990 |
| WO | 91/18856 | 12/1991 |
| WO | 92/03401 | 3/1992 |
| WO | 92/12946 | 8/1992 |
| WO | 93/06039 A1 | 4/1993 |
| WO | 93/16798 | 9/1993 |
| WO | 96/22263 | 7/1996 |
| WO | WO 96/00696 † | 11/1996 |
| WO | 97/44302 | 11/1997 |
| WO | 98/12165 | 3/1998 |
| WO | 99/07443 | 2/1999 |
| WO | 00/07718 A1 | 2/2000 |
| WO | 00/09261 A1 | 2/2000 |
| WO | 01/14300 A1 | 3/2001 |
| WO | 01/38275 A1 | 5/2001 |
| WO | 01/44149 A1 | 6/2001 |
| WO | 02/094749 A1 | 11/2002 |
| WO | 02/094750 A1 | 11/2002 |
| WO | 02/094751 A2 | 11/2002 |
| WO | 02/094752 A1 | 11/2002 |
| WO | 03/000635 A1 | 1/2003 |
| WO | 03/002251 A2 | 1/2003 |
| WO | 03/018524 A1 | 3/2003 |
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/104689 A2 | 11/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006/067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/083427 A2 | 8/2006 |
| WO | 2006/100312 A2 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/071046 A1 | 6/2007 |
| WO | 2007/079038 A2 | 7/2007 |
| WO | 2007/091009 A2 | 8/2007 |
| WO | 2007/094995 A2 | 8/2007 |
| WO | 2007/107031 A1 | 9/2007 |
| WO | 2007/111997 A2 | 10/2007 |
| WO | 2007/114479 A1 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |
| WO | 2008/036562 A1 | 3/2008 |
| WO | 2008/036563 A2 | 3/2008 |
| WO | 2008/106318 A1 | 9/2008 |
| WO | 2008/106319 A1 | 9/2008 |
| WO | 2008/157043 A1 | 12/2008 |
| WO | 2008/157044 A1 | 12/2008 |
| WO | 2008/157045 A1 | 12/2008 |
| WO | 2008/157046 A1 | 12/2008 |

(56) References Cited

FOREIGN PATENT DOCUMENTS

| WO | 2008/157047 A1 | 12/2008 |
|---|---|---|
| WO | 2009/152403 A1 | 12/2009 |
| WO | 2009/152405 A1 | 12/2009 |
| WO | 2009/152408 A1 | 12/2009 |
| WO | 2010/009376 A1 | 1/2010 |
| WO | 2011/008573 A1 | 1/2011 |
| WO | 2011/109244 A2 | 9/2011 |
| WO | 2011/159490 A1 | 12/2011 |

OTHER PUBLICATIONS

U.S. Office Communication from U.S. Appl. No. 10/826,885 dated Oct. 31, 2005.
U.S. Office Communication from U.S. Appl. No. 10/826,885 dated Apr. 19, 2006.
U.S. Office Communication from U.S. Appl. No. 10/826,885 dated Jul. 27, 2006.
U.S. Office Communication from U.S. Appl. No. 10/826,885 dated Nov. 2, 2006.
U.S. Office Communication from U.S. Appl. No. 10/826,885 dated Jan. 24, 2007.
U.S. Office Communication from U.S. Appl. No. 10/893,418 dated Jun. 14, 2007.
U.S. Office Communication from U.S. Appl. No. 10/893,418 dated Jan. 2, 2008.
U.S. Office Communication from U.S. Appl. No. 11/091,130 dated Oct. 3, 2007.
U.S. Office Communication from U.S. Appl. No. 11/101,886 dated Jan. 24, 2007.
U.S. Office Communication from U.S. Appl. No. 11/254,438 dated Jan. 24, 2007.
U.S. Office Communication from U.S. Appl. No. 11/254,438 dated Nov. 1, 2007.
U.S. Office Communication from U.S. Appl. No. 11/778,479 dated Feb. 22, 2010.
U.S. Office Communication from U.S. Appl. No. 12/112,926 dated Jan. 16, 2009.
U.S. Office Communication from U.S. Appl. No. 12/112,926 dated Sep. 14, 2009.
U.S. Office Communication from U.S. Appl. No. 12/112,926 dated Jan. 7, 2010.
U.S. Office Communication from U.S. Appl. No. 12/112,926 dated Jul. 22, 2010.
U.S. Office Communication from U.S. Appl. No. 12/112,926 dated Jan. 7, 2011.
U.S. Office Communication from U.S. Appl. No. 12/123,924 dated Mar. 19, 2010.
U.S. Office Communication from U.S. Appl. No. 12/123,924 dated Aug. 30, 2010.
U.S. Office Communication from U.S. Appl. No. 12/139,135 dated Nov. 24, 2010.
U.S. Office Communication from U.S. Appl. No. 12/502,024 dated Oct. 26, 2010.
U.S. Office Communication from U.S. Appl. No. 12/715,526 dated Feb. 17, 2011.
U.S. Office Communication from U.S. Appl. No. 12/139,135 dated Apr. 14, 2011.
U.S. Office Communication from U.S. Appl. No. 12/715,526 dated May 24, 2011.
U.S. Office Communication from U.S. Appl. No. 12/502,024 dated May 31, 2011.
U.S. Office Communication from U.S. Appl. No. 12/139,135 dated Oct. 14, 2011.
U.S. Office Communication from U.S. Appl. No. 12/477,307 dated Oct. 7, 2011.
U.S. Office Communication from U.S. Appl. No. 12/477,319 dated Jul. 22, 2011.
U.S. Office Communication from U.S. Appl. No. 12/502,024 dated Sep. 16, 2011.
U.S. Office Communication from U.S. Appl. No. 12/477,307 dated Feb. 27, 2012.
U.S. Office Communication from U.S. Appl. No. 12/715,526 dated Jan. 4, 2012.
Abstract of BE 812868, Aromatic hydrocarbons prodn. from chlorinated hydrocarbons, Publication date: Sep. 27, 1974, esp@cenet database—worldwide.
Abstract of BE 814900, Volatile aramatic cpds. prodn., Publication date: Sep. 2, 1974, esp@cenet database—worldwide.
Abstract of BR 0210054, Oxidative halogenation of C1 hydrocarbons to halogenated C1 hydrocarbons and integrated processes related thereto, Publication date: Aug. 17, 2004, Inventor: Schweizer et al., esp@cenet database—worldwide.
Abstract of CA 2447761 A1, Oxidative halogenation of C1 hydrocarbons to halogenated C1 hydrocarbons and integrated processes related thereto, Publication date: Nov. 28, 2002, Inventor: Hickman, et al.
Abstract of CA 2471295 A1, Integrated process for synthesizing alcohols, ethers, and olefins from alkanes, Publication date: Jul. 31, 2003, Inventor: Sherman et al.
Abstract of CN 1199039, Pentanol and its production process, Publication date: Nov. 18, 1998, Inventor: Kailun, esp@cenet database—worldwide.
Abstract of CN 1210847, Process for producing low carbon alcohol by directly hydrating low carbon olefines, Publication date: Mar. 17, 1999, Inventor: Zhenguo et al., esp@cenet database—worldwide.
Abstract of CN 1321728, Method for preparing aromatic hydrocarbon and hydrogen gas by using law-pressure gas, Publication date: Nov. 14, 2001, Inventor: Jie et al., esp@cenet database—worldwide.
Abstract of CN 1451721, Process for non-catalytic combustion deoxidizing coal mine gas for producing methanol, Publication date: Oct. 29, 2003, Inventor: Pengwan et al., esp@cenet database—worldwide.
Abstract of CN 1623969, Method for preparing 1, 4-benzene dimethanol, Publication date: Jun. 8, 2005, Inventor: Jiarong et al., esp@cenet database—worldwide.
Abstract of CN 1657592, Method for converting oil to multiple energy fuel product, Publication date: Aug. 24, 2005, Inventor: Li, esp@cenet database—worldwide.
Abstract of CN 1687316, Method for producing biologic diesel oil from rosin, Publication date: Oct. 26, 2005, Inventor: Jianchun et al., esp@cenet database—worldwide.
Abstract of CN 1696248, Method for synthesizing biologic diesel oil based on ion liquid, Publication date: Nov. 16, 2005, Inventor: Sun, esp@cenet database—worldwide.
Abstract of CN 1699516, Process for preparing bio-diesel-oil by using miroalgae fat, Publication date: Nov. 23, 2005, Inventor: Miao, esp@cenet database—worldwide.
Abstract of CN 1704392, Process for producing alkylbenzene, Publication date: Dec. 7, 2005, Inventor: Gao, esp@cenet database—worldwide.
Abstract of CN 1724612, Biological diesel oil catalyst and method of synthesizing biological diesel oil using sai catalyst, Publication date: Jan. 25, 2006, Inventor: Gu, esp@cenet database—worldwide.
Abstract of CN 1986737, Process for producing biodiesel oil with catering waste oil, Publication date: Jun. 27, 2007, Inventor: Chen, esp@cenet database—worldwide.
Abstract of CN 100999680, Esterification reaction tech. of preparing biodiesel by waste oil, Publication date: Jul. 18, 2007, Inventor: Weiming, esp@cenet database—worldwide.
Abstract of CN 101016229, Refining method for bromomeoamyl alcohol, Publication date: Aug. 15, 2007, Inventor: Tian, esp@cenet database—worldwide.
Abstract of DE 3209964, Process for the preparation of chlorinated hydrocarbons, Publication date: Nov. 11, 1982, Inventor: Pyke et al., esp@cenet database—worldwide.
Abstract of DE 3210196, Process for the preparation of a monochlorinated olefin, Publication date: Jan. 5, 1983, Inventor: Pyke et al., esp@cenet database—worldwide.
Abstract of DE 3226028, Process for the preparation of monochlorinated olefin, Publication date: Feb. 3, 1983, Inventor: Pyke et al., esp@cenet database—worldwide.

(56) References Cited

OTHER PUBLICATIONS

Abstract of DE 3334225, Process for the preparation of 1,2-dichloroethane, Publication date: Apr. 4, 1985, Inventor: Hebgen et al, esp@cenet database—worldwide.
Abstract of DE 4232056, 2,5-Di:methyl-hexane-2,5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.
Abstract of DE 4434823, Continuous prodn. of hydroxy-benzyl alkyl ether, Publication date: Apr. 4, 1996, Inventor: Stein et al., esp@cenet database—worldwide.
Abstract of EP 0021497 (A1),Synthesis of polyoxyalkylene glycol monoalkyl ethers.; Publication date: Jan. 7, 1981, Inventor: Gibson, esp@cenet database—worldwide.
Abstract of EP 0039471, Process for the preparation of 2-chloro-1,1,1,2,3,3,3-heptafluoropropane., Publication date: Nov. 11, 1981, Inventor: Von Halasz, esp@cenet database—worldwide.
Abstract of EP 0101337, Process for the production of methylene chloride., Publication date: Feb. 22, 1984, Inventor: Olah et al., esp@cenet database—worldwide.
Abstract of EP 0235110, Process for the stabilization of silicalite catalysts., Publication date: Sep. 2, 1987, Inventor: Debras et al., esp@cenet database—worldwide.
Abstract of EP 0407989, Method for the production of 1,1,1-trifluoro-2,2-dichloroethane by photochlorination., Publication date: Jan. 16, 1991, Inventor: Cremer et al., esp@cenet database—worldwide.
Abstract of EP 0442258, Process for the preparation of a polyunsaturated olefin., Publication date: Aug. 21, 1991, Inventor: Gaudin et al., esp@cenet database, worldwide.
Abstract of EP 0465294, Process for the preparation of unsaturated bromides., Publication date: Jan. 8, 1992, Inventor: Decaudin et al., esp@cenet database—worldwide.
Abstract of EP 0549387, Synthesis of n-perfluorooctylbromide., Publication date: Jun. 30, 1993, Inventor: Drivon et al., esp@cenet database—worldwide.
Abstract of EP 0850906, Process and apparatus for the etherification of olefinic hydrocarbon feedstocks, Publication date: Jul. 1, 1998, Inventor: Masson, esp@cenet database—worldwide.
Abstract of EP 0858987, Process for conversion of lighter alkanes to higher hydrocarbons, Publication date: Aug. 19, 1998, Inventor: Amariglio, et al., esp@cenet database—worldwide.
Abstract of EP 1395536, Oxidative halogenation of C1 hydrocarbons to halogenated C1 hydrocarbons and integrated processes related thereto, Publication date: Mar. 10, 2004, Inventor: Schweizer et al., esp@cenet database—worldwide.
Abstract of EP 1404636, Integrated process for synthesizing alcohols and ethers from alkanes, Publication date: Apr. 7, 2004, Inventor: Zhou et al., esp@cenet database—worldwide.
Abstract of EP 1435349 A2, Integrated process for synthesizing alcohols and ethers from alkanes, Publication date: Jul. 7, 2004, Inventor: Zhou et al.
Abstract of EP 1474371, Integrated process for synthesizing alcohols, ethers, and olefins from alkanes, Publication date: Nov. 10, 2004, Inventor: Zhou et al., esp@cenet database—worldwide.
Abstract of FR 2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR 2880019, Manufacturing 1,2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR 2883870, Formation of 1,2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.
Abstract of FR 2883871, Preparing 1,2-dichloroethane comprises cracking hydrocarbon to form mixture, sending mixture into storage reservoir, supplying mixture into chlorination and/or oxychloration reactor, and separating 1,2-dichloroethane from reactor, Publication date: Oct. 6, 2006, Inventor: Balthasart et al., esp@cenet database—worldwide.
Abstract of IT 1255246, Process for the preparation of dinitrodiphenylmethanes, Publication date: Oct. 20, 1995, Applicant: Enichem Spa et al., esp@cenet database—worldwide.
Abstract of IT 1255358, Process for the synthesis of 1,4-butanediol, Publication date: Oct. 31, 1995, Inventor: Ricci Marco, esp@cenet database—worldwide.
Abstract of JP 2142740, Production of fluoroalcohol, Publication date: May 31, 1990, Inventor: Tsutomu et al., esp@cenet database—worldwide.
Abstract of JP 2144150, Chemical process and catalyst used therefore, Publication date: Jun. 1, 1990, Inventor: Deidamusu et al., esp@cenet database—worldwide.
Abstract of JP 4305542, Production of halogenated hydrocarbon compounds, Publication date: Oct. 28, 1992, Inventor: Shinsuke et al., esp@cenet database—worldwide.
Abstract of JP 6172225, Method for fluorinating halogenated hydrocarbon, Publication date: Jun. 21, 1994, Inventor: Takashi et al., esp@cenet database—worldwide.
Abstract of JP 6206834, Production of Tetrachloroethanes, Publication date: Jul. 26, 1994, Inventor: Toshiro et al., esp@cenet database—worldwide.
Abstract of JP 8266888, Method for decomposing aromatic halogen compound, Publication date: Oct. 15, 1996, Inventor: Yuuji et al., esp@cenet database—worldwide.
Abstract of JP 2001031605, Production of 3-hydroxy-1-cycloalkene, Publication date: Feb. 6, 2001, Inventor: Hideo et al., esp@cenet database—worldwide.
Abstract of JP 2004-529189.
Abstract of JP 2004075683, Method for producing optically active halogenohydroxypropyl compound and glycidyl compound, Publication date: Mar. 11, 2004, Inventor: Keisuke et al., esp@cenet database—worldwide.
Abstract of JP 2004189655, Method for fluorinating with microwave, Publication date: Jul. 8, 2004, Inventor: Masaharu et al., esp@cenet database—worldwide.
Abstract of JP 2005075798, Method for producing adamantyl ester compound, Publication date: Mar. 24, 2005, Inventor: Norihiro et al., esp@cenet database—worldwide.
Abstract of JP 2005082563, Method for producing 1,3-adamantanediol, Pbblication date: Mar. 31, 2005, Inventor: Norihiro et al., esp@cenet database—worldwide.
Abstract of JP 2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP 2005254092, Method of manufacturing alkynes, Publication date: Sep. 22, 2005, Inventor: Shirakawa Eiji, esp@cenet database—worldwide.
Abstract of JP 2006151892, Preparation method of alcohol derivative, Publication date: Jun. 15, 2006, Inventor: Baba Akio et al., esp@cenet database—worldwide.
Abstract of JP 2006152263, Organic-inorganic hybrid-type mesoporous material, method for producing the same, and solid catalyst, Publication date: Jun. 15, 2006, Inventor: Junko et al., esp@cenet database—worldwide.
Abstract of JP 2006193473, Aryl polyadamantane derivative having carboxy or acid anhydride group and method for producing the same, Publication date: Jul. 27, 2006, Inventor: Yasuto et al, esp@cenet database—worldwide.
Abstract of JP 2006231318, Phosphorus containing macromolecule immobilizing palladium catalyst and method for using the same, Publication date: Sep. 7, 2006, Inventor: Osamu et al., esp@cenet database—worldwide.

(56) References Cited

OTHER PUBLICATIONS

Abstract of JP 2006263567, Optical resolution method of optical isomer and optical resolution device, Publication date: Oct. 5, 2006, Inventor: Yoshikazu et al., esp@cenet database—worldwide.

Abstract of JP 2006265157, Method for catalytically activating silicated nucleating agent using phosphazene base, Publication date: Oct. 5, 2006, Inventor: Yoshinori et al., esp@cenet database—worldwide.

Abstract of JP 2006306758, Method for producing biaryl compound, Publication date: Nov. 9, 2006, Inventor: Yuji et al., esp@cenet database—worldwide.

Abstract of JP 2007001942, Production method of para-xylene, Publication date: Jan. 11, 2007, Inventor: Kazuyoshi, esp@cenet database—worldwide.

Abstract of JP 2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.

Abstract of JP 2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.

Abstract of JP 2007061594, Method for decomposing organohalogen compound and mobile decomposition system, Publication date: Mar. 15, 2007, Inventor: Koichi et al., esp@cenet database—worldwide.

Abstract of JP 2007099729, Method for producing alpha-methylstyrene or cumene, Publication date: Apr. 19, 2007, Inventor: Toshio, esp@denet database—worldwide.

Abstract of RO 119778, Process for preparing perchloroethylene, Publication date: Mar. 30, 2005, Inventor: Horia et al., esp@cenet database—worldwide.

Abstract of WO 0105737, Method for preparing a carboxylic acid, Publication date: Jan. 25, 2001, Inventor: Pascal et al., esp@cenet database—worldwide.

Abstract of WO 0105738, Method for Preparing a carboxylic acid, Publication date: Jan. 25, 2001, Inventor: Pascal et al., esp@cenet database—worldwide.

Abstract of WO 9721656, Method for making fluoroalkanols, Publication date: Jun. 19, 1997, Inventor: Gillet, esp@cenet database—worldwide.

Abstract of WO 9950213, Method for producing dialkyl ethers, Publication date: Oct. 7, 1999, Inventor: Falkowski et al., esp@cenet database—worldwide.

Abstract of WO 2004092099, Method for producing cyclic enols, Publication date: Oct. 28, 2004, Inventor: Friedrich Marko et al., esp@cenet database—worldwide.

Abstract of WO 2006063852, Electroluminescent polymers and use thereof, Publication date: Jun. 22, 2006, Inventor: Buesing Arne et al., esp@denet database—worldwide.

Abstract of WO 2006076942, Method for the production of synthetic fuels from oxygenates, Publication date: Jul. 27, 2006, Inventor: Rothaemel et al., esp@cenet database—worldwide.

Abstract of WO 2006136135, Method for decarboxylating C—C cross-linking of carboxylic acids with carbon electrophiles, Publication date: Dec. 28, 2006, Inventor: Goossen Lukas et al., esp@cenet database—worldwide.

Abstract of WO 2007028761, Method for chlorinating alcohols, Publication date: Mar. 15, 2007, Inventor: Rohde et al., esp@cenet database—worldwide.

Abstract of WO 2007128842, Catalytic transalkylation of dialkyl benzenes, Publication date: Nov. 15, 2007, Inventor: Goncalvesalmeida et al., esp@cenet database—worldwide.

Abstract of WO 2007137566, Method for catalytic conversion of organic oxygenated compounds from biomaterials, Publication date: Dec. 6, 2007, Inventor: Reschetilowski, esp@cenet database—worldwide.

Adachi et al., Synthesis of sialyl lewis X ganglioside analogs containing a variable length spacer between the sugar and lipophilic moieties, J. Carbohydrate Chemistry, vol. 17, No. 4-5, 1998, pp. 595-607, XP009081720.

Akhrem et al., Ionic Bromination of Ethane and other alkanes (cycloalkanes) with bromine catalyzed by the polyhalomethane-2AlBr3 aprotic organic superacids under mild conditions, Tetrahedron Letters, vol. 36, No. 51, 1995, pp. 9365-9368, Pergamon, Great Britain.

Bagno et al., Superacid-catalyzed carbonylation of methane, methyl halides, methyl alcohol, and dimethyl ether to methyl acetate and acetic acid, J. Org. Chem. 1990, 55, pp. 4284-4289, Loker Hydrocarbon Research Institute; University of Southern California.

Bakker et al., An exploratory study of the addition reactions of ethyleneglycol, 2-chloroethanol and 1,3-dichloro-2-propanol to 1-dodecene, J. Am. Oil Chem. Soc., vol. 44, No. 9, 1967, pp. 517-521, XP009081570.

Benizri et al., Study of the liquid-vapor equilibrium in the bromine-hydrobromic acid-water system, Hydrogen Energy Vector, 1980, pp. 101-116.

Bouzide et al., Highly selective silver (I) oxide mediated monoprotection of symmetrical diols, Tetrahedron Letters, Elsevier, vol. 38, No. 34, 1997, pp. 5945-5948, XP004094157.

Bradshaw et al., Production of hydrobromic acid from bromine and methane for hydrogen production, Proceedings of the 2001 DOE Hydrogen Program Review, NREL/CP-570-30535, 2001, pp. 1-8.

Chang et al., The conversion of methanol and other O-compounds to hydrocarbons over zeolite catalysts, Journal of Catalysis 47, 1977, Academic Press, Inc., pp. 249-259.

Claude et al., Monomethyl-branching of long n-alkanes in the range from decane to tetracosane on Pt/H-ZSM-22 bifunctional catalyst, Journal of Catalysis 190, 2000, pp. 39-48.

Combined International Search Report and Written Opinion dated Apr. 17, 2007 for PCT/US2006/013394, Applicant: GRT, Inc. , pp. 1-13.

Driscoll, Direct methane conversion, Federal Energy Technology Center, U.S. Department of Energy, M970779, pp. 1-10.

Fenelonov, et al., Changes in texture and catalytic activity of nanocrystalline MgO during its transformation to MgCl2 in the reaction with 1-chlorobutane, J. Phys. Chem. B 2001, 105, 2001 American Chemical Society, pp. 3937-3941.

Final Report, Abstract, http://chemelab.ucsd.edu/methanol/memos/final.html, May 9, 2004, pp. 1-7.

Gibson, Phase-transfer synthesis of monoalkyl ethers of oligoethylene glycols, J. Org. Chem. 1980, vol. 45, No. 6, pp. 1095-1098, XP002427776.

http://webbook.nist.gov/, Welcome to the NIST chemistry webbook, Sep. 10, 2007, U.S. Secretary of Commerce on Behalf of the United States of America, pp. 1-2.

Ione, et al., Syntheses of hydrocarbons from compounds containing one carbon atom using bifunctional zeolite catalysts, Solid Fuel Chemistry, Khimiya Tverdogo Topliva, 1982, Allerton Press, Inc., vol. 16, No. 6, pp. 29-43.

Jaumain et al., Direct catalytic conversion of chloromethane to higher hydrocarbons over various protonic and cationic zeolite catalysts as studied by in-situ FTIR and catalytic testing, Studies in Surface Science and Catalysis 130, Elsevier Science B.V., 2000, pp. 1607-1612.

JLM Technology Ltd., The Miller GLS Technology for conversation of light hydrocarbons to alcohols, New Science for the Benefit of Humanity, May 31, 2000; pp. 1-10.

Kirk-Othmer, Encyclopedia of Chemical Technology, 4th Edition, vol. 1, A Wiley-Interscience Publication, John Wiley & Sons, 1991, pp. 946-997.

Liu et al., Higher hydrocarbons from methane condensation mediated by HBr, Journal of Molecular Catalysis A: Chemical 273, Elsevier B.V., 2007, pp. 14-20.

Loiseau et al., Multigram synthesis of well-defined extended bifunctional polyethylene glycol (PEG) chains, J. Org. Chem., vol. 69, No. 3, XO-002345040, 2004, pp. 639-647.

Lorkovic et al., A novel integrated process for the functionalization of methane and ethane: bromine as mediator, Catalysis Today 98, 2004, pp. 317-322.

(56) References Cited

OTHER PUBLICATIONS

Lorkovic et al., C1 oxidative coupling via bromine activation and tandem catalytic condensation and neutralization over CaO/zeolite composites II. Product distribution variation and full bromine confinement, Catalysis Today 98, 2004, pp. 589-594.
Lorkovic et al., C1 coupling via bromine activation and tandem catalytic condensation and neutralization over CaO/zeolite composites, Chem. Comm. 2004, pp. 566-567.
Mihai, et al., Application of Bronsted-type LFER in the study of the phospholipase C Mechanism, J. Am. Chem. Soc., vol. 125, No. 11, XP-002427777, 2003, pp. 3236-3242.
Mishakov et al., Nanocrystalline MgO as a dehydrohalogenation catalyst, Journal of Catalysis 206, Elsevier Science, USA, 2002, pp. 40-48.
Mochida, et al., The catalytic dehydrohalogenation of haloethanes on solid acids and bases, Bulletin of the Chemical Society of Japan, vol. 44, Dec. 1971, pp. 3305-3310.
Motupally et al., Recycling chlorine from hydrogen chloride, The Electrochemical Society Interface, Fall 1998, pp. 32-36.
Murray et al., Conversion of methyl halides to hydrocarbons on basic zeolites: a discovery by in situ NMR, J. Am. Chem. Soc., 1993, vol. 115, pp. 4732-4741.
Nishikawa et al., Ultrasonic relaxations in aqueous solutions of alcohols and the balance between hydrophobicity and hydrophilicity of the solutes, J. Phys. Chem., vol. 97, No. 14, XP-002427775, 1993, pp. 3539-3544.
Olah et al., Antimony pentafluoride/graphite catalyzed oxidative carbonylation of methyl halides with carbon monoxide and copper oxides (or copper/oxygen) to methyl acetate, J. Org. Chem. 1990, 55, pp. 4293-4297.
Olah et al., Antimony pentafluoride/graphite catalyzed oxidative conversion of methyl halides with copper oxides (or copper/oxygen) to dimethyl ether, J. Org. Chem. 1990, 55, pp. 4289-4293.
Olah, Electrophilic methane conversion, American Chemical Society, Acc. Chem. Res. 1987, 20, pp. 422-428.
Olah, Hydrocarbons through methane derivatives, Hydrocarbon Chemistry, 1995, pp. 89-90, John Wiley & Sons, Inc.
Olah et al., Hydrocarbons through methane derivatives, Hydrocarbon Chemistry, 2nd Edition, 2003, pp. 123, 149, and 153, John Wiley & Sons, Inc.
Olah et al., Onium Ylide Chemistry. 1. Bifunctional acid-base-catalyzed conversion of heterosubstituted methanes into ethylene and derived hydrocarbons. The Onium Ylide mechanism of the C1—C2 conversion. J. Am. Chem. Soc. 1984, 106, pp. 2143-2149.
Olah et al., Selective monohalogenation of methane over supported acid or platinum metal catalysts and hydrolysis of methyl halides over y-alumina-supported metal oxide/hydroxide catalysts. A feasible path for the oxidative conversion of methane into methyl alcohol/dimethyl ether., J. Am. Chem. Soc. 1985, 107, pp. 7097-7105.
Prelog et al., 234. Chirale 2, 2'-polyoxaalkano-9,9'-spirobifluorene, Helvetica Chimica Acta, vol. 62, No. 7, 1979 pp. 2285-2302.
Rakoff et al., Quimica Organica Fundamental, Organic Chemistry, The Macmillan Company, 1966, pp. 58-63 and 76-77.
Richards, et al., Nanocrystalline ultra high surface area magnesium oxide as a selective base catalyst, Scripta Materialia, 44, 2001, pp. 1663-1666, Elsevier Science Ltd.
Shimizu et al., Gas-Phase electrolysis of hydrobromic acid using PTFE-bonded carbon electrode, Int. J. Hydrogen Energy, vol. 13, No. 6, pp. 345-349, 1988.
Smirnov et al., Selective bromination of alkanes and arylalkanes with CBr4, Mendeleev Commun., 2000, pp. 175-176.
Sun et al., Nanocrystal metal oxide—Chlorine adducts: selective catalysts for chlorination of alkanes, J. Am. Chem. Soc., 1999, 121, pp. 5587-5588.
Sun et al., A general integrated process for synthesizing olefin oxides, Chem. Commun., The Royal Society of Chemistry 2004 pp. 2100-2101.
Tamura et al., The reactions of grignard reagents with transition metal halides: Coupling, disproportionation, and exchange with olefins, Bulletin of the Chemical Society of Japan, vol. 44, Nov. 1971, pp. 3063-3073.
Taylor et al., Direct conversion of methane to liquid hydrocarbons through chlorocarbon intermediates, 1988, Elsevier Science Publishers B.V. Amsterdam, Netherlands, pp. 483-489.
Taylor, Conversion of substituted methanes over ZSM-catalysts, 2000, pp. 3633-3638, Studies in Surface Science and Catalysis 130, Elsevier Science B.V.
Taylor, PETC's on-site naural gas conversion efforts, Preprints of the Fuel Division, 208th National Meeting of the American Chemical Society, 39 (4), 1994, pp. 1228-1232.
Thomas et al., Catalytically active centres in porous oxides: design and performance of highly selective new catalysts, Chem. Commun., 2001, pp. 675-687.
Thomas et al., Synthesis and characterization of a catalytically active nickel-silicoaluminophosphate catalyst for the conversion of methanol to ethene, American Chemical Society, 1991, 3, pp. 667-672.
Van Velzen et al., HBr electrolysis in the Ispra mark 13A flue gas desulphurization process: electrolysis in a DEM cell, Journal of Applied Electrochemistry, 20, 1990, pp. 60-68.
Wagner et al., Reactions of VX, GD, and HD with nanosize CaO: autocatalytic dehydrohalogenation of HD, J. Phys. Chem. B 2000, 104, pp. 5118-5123, 2000 American Chemical Society.
Wauters et al., Electrolytic membrane recovery of bromine from waste hydrogen bromide streams, AIChE Journal, Oct. 1998, vol. 44, No. 10, pp. 2144-2148.
Weissermel et al., Industrial Organic Chemistry, 3rd Edition, 1997, pp. 160-162, and 208.
Whitesides et al., Nuclear magnetic resonance spectroscopy. The effect of structure on magnetic nonequivalence due to molecular asymmetry, J. Am. Chem. Soc., vol. 86, No. 13, 1964, pp. 2628-2634, XP002427774.
Yilmaz et al., Bromine mediated partial oxidation of ethane over nanostructured zirconia supported metal oxide/bromide, Microporous and Mesoporous Materials, 79, 2005, Science Direct, Elsevier, pp. 205-214.
Zhou et al., An integrated process for partial oxidation of alkanes, Chem. Commun., 2003, The Royal Society of Chemistry, pp. 2294-2295.
ZSM-5 Catalyst, http://chemelba.ucsd.edu/methanol/memos/ZSM-5.html, Nov. 6, 2003, p. 1.
Abstract of GB 998681(A), Improvements in or relating to the recovery of bromine from bromine-containing materials, Publication date: Jul. 21, 1965, Applicant: Electro Chimie Metal+, espacenet worldwide database.
Abstract of JP 55-073619, Condensation of methyl chloride through dehydrochlorination, Publication date: Jun. 3, 1980, Inventor: Shigeo et al., http://www19.ipdl.inpit.go.jp/PA1/result. . . .
Hannus, Adsorption and transformation of halogenated hydrocarbons over zeolites, Applied Catalysis A: General 189, 1999, XP-002634422, pp. 263-276.
Howe, Zeolite catalysts for dehalogenation processes, Applied Catalysis A: General 271, 2004, XP-002634421, pp. 3-11.
Li et al., Pyrolysis of Halon 1301 over zeolite catalysts, Microporous and Mesoporous Materials 35-36, 2000, XP-002634423, pp. 219-226.
Chretien; Process for the Adjustment of the HHV in the LNG Plants; 23rd World Gas Conference; Amsterdam 2006; Jun. 5-9, 2006; pp. 1-14.
Yang et al.; Maximising the Value of Surplus Ethane and Cost-Effective Design to Handle Rich LNG; publ. date Jun. 1, 2007; pp. 1-13.
Jack F. Mills, "Bromine" in Ullmann's Encyclopedia of Industrial Chemistry, Fifth, Completely Revised Edition, vol. A4, pp. 391 and 397, published 1985, VCH Verlagsgesellschaft mbH, Federal Republic of Germany.†
Philip F. Jackisch, "Bromine" in Kirk-Othmer Encyclopedia of Chemical Technology, Fourth Edition, vol. 4, pp. 536, 548, 549, 550, and 560, published 1992, John Wiley & Sons, United States of America.†

(56) References Cited

OTHER PUBLICATIONS

Dr. Miri Kesner, "How is Bromine Produced" in Bromine and Bromine Compounds from the Dead Sea, Israel Products in the Service of People, pp. 3, 5, 78, and 87, first published in Hebrew in Israel in 1999 by The Department of Science Teaching, The Weizmann Institute of Science.†
Henshuiinkai, Kagaku Daijiten; Kagaku Daijiten 4, Japan, Kyoritsu Publisher, Oct. 15, 1963; pp. 652-654.
Jacobson, C.A.; "Encyclopedia of Chemical Reactions"; vol. 1, 1946, pp. 722.
U.S. Office Communication from U.S. Appl. No. 12/792,335, dated Aug. 17, 2012.
U.S. Office Communication from U.S. Appl. No. 12/957,036 dated Aug. 16, 2012.
U.S. Office Communication from U.S. Appl. No. 13/157,584 dated May 11, 2012.
U.S. Office Communication from U.S. Appl. No. 13/157,584 dated Aug. 29, 2012.
U.S. Appl. No. 60/487,364, filed Jul. 15, 2003, Lorkovic et al.
U.S. Appl. No. 60/559,844, filed Apr. 6, 2004, Sherman et al.
U.S. Appl. No. 60/765,115, filed Feb. 3, 2006, Gadewar et al.
Abstract of JP publication No. 08-283182, Production of Hydrochloromethanes, Publication date: Oct. 29, 1996, Inventor: Kojiro et al.; http://www19/ipdlinpit.go.jp . . . .
U.S. Office Communication from U.S. Appl. No. 12/792,335, dated Jan. 2, 2013.
U.S. Office Communication from U.S. Appl. No. 13/117,785 dated Mar. 14, 2013.
U.S. Office Communication from U.S. Appl. No. 13/117,785 dated Apr. 22, 2013.
U.S. Office Communication from U.S. Appl. No. 13/173,847 dated Sep. 6, 2013.
U.S. Office Communication from U.S. Appl. No. 13/212,291 dated May 10, 2013.
U.S. Office Communication from U.S. Appl. No. 13/269,683 dated Jun. 6, 2013.
U.S. Office Communication from U.S. Appl. No. 13/647,002 dated Jun. 5, 2013.
Lewis, Richard J. Sr., (2007); Hawley's Condensed Chemical Dictionary (15th Edition); John Wiley & Sons; p. 181.
U.S. Office Communication from U.S. Appl. No. 13/173,847 dated Jan. 21, 2014.
U.S. Office Communication from U.S. Appl. No. 13/679,600 dated Jan. 17, 2014.
U.S. Office Communication from U.S. Appl. No. 13/705,106 dated Feb. 3, 2014.
U.S. Office Communication from U.S. Appl. No. 13/713,926 dated Jan. 30, 2014.
U.S. Office Communication from U.S. Appl. No. 13/760,291 dated Apr. 4, 2014.
U.S. Office Communication from U.S. Appl. No. 12/139,135 dated Nov. 7, 2013.
Morgan et al., "The Effect of pH on the Kinetics of Spontaneous Fe(II) Oxidation by O2 in Aqueous Solution—Basic Principles and a Simple Heuristic Description", Chemosphere, 68 (2007), p. 2080-2084.
U.S. Office Communication from U.S. Appl. No. 12/139,135 dated Jun. 19, 2014.
U.S. Office Communication from U.S. Appl. No. 13/705,111 dated Jul. 3, 2014.
U.S. Office Communication from U.S. Appl. No. 13/713,926 dated Jul. 7, 2014.

\* cited by examiner
† cited by third party

PROCESSES AND SYSTEMS FOR DRYING LIQUID BROMINE

BACKGROUND OF THE INVENTION

The present invention relates to processes and systems for drying wet bromine liquid, and more particularly, in one or more embodiments, to processes and systems for drying wet bromine liquid in a system having two fractionators, one for separating substantially dry bromine from wet bromine liquid and another for separating substantially pure water from water having bromine dissolved therein.

Bromine has a wide variety of industrial uses, including in the preparation of disinfectants, chemical flame retardants, and photographic materials, in water purification processes, and as an intermediate in the manufacture of dyestuffs, drugs, resins and refrigerants. Bromine may also be used in the bromination of alkanes to produce alkyl bromides that in turn have uses in processes, such as the production of higher molecular weight hydrocarbons useful as chemical intermediates and as blending stock or fuels. Many of the uses prefer dry bromine containing less than 5 wppm water.

Wet bromine is highly corrosive and requires that components used to handle wet bromine be constructed of corrosion-resistant materials or coatings, such as tantalum, which are extremely expensive. As dry bromine is much less corrosive than wet bromine, it usually is advantageous to use dry bromine in most industrial processes employing bromine.

Some processes that have been proposed for drying bromine utilize a drying agent for the adsorption of water therefrom. However, the use of a drying agent is accompanied by many drawbacks. If the drying agent is a solid, for example an inorganic salt, solid incrustations form on the surface of the drying agent rendering the surface impermeable and therefore decreasing the efficiency of the drying agent. When liquid drying agents are used, for instance sulfuric acid, bromine may become contaminated with components of the drying agents. Another drawback in using drying agents is that the drying agent must be regenerated or additional fresh drying agent must be added or used at varying intervals.

In accordance with another process, liquid bromine having a water and chlorine content is kept at about its boiling point, gradually loses water and chlorine and over a period of time to drop the water and chlorine content to lower levels. While this process produces bromine with reduced water and chlorine content, it is not deemed commercially practical as keeping the bromine liquid at the boiling point causes significant loss of bromine with the evaporated water and chlorine. In addition, for large flow rates of bromine, the long residence time needed for this process requires large bromine storages which present tremendous hazard risk. Furthermore, this process does not achieve requisite low levels of water and chlorine.

Liquid crude bromine containing impurities, such as water and chlorine, is vaporized and heated to greater than 700° F. in accordance with another process, added to steam and condensed to form water and liquid bromine. The liquid bromine is separated from water and dried over concentrated sulfuric acid. The dried bromine is then distilled to remove its heavy end contaminants. The purified bromine produced having an overall purity of 99.98 percent or better, i.e. less than 200 wppm of overall impurities. Chlorine<30 wppm; organic material<30 wppm; water<30 wppm; and HCl<2° wppm; nonvolatile residue<60 wppm. Bromine dried by this process still contains a moisture level not low enough to prevent corrosion at elevated temperatures. Also, the process generates a dilute sulfuric acid solution which is a waste stream requiring disposal.

Thus, a need exists for processes and systems for drying liquid bromine without the use of drying agents and their attendant problems which is economical, results in two streams of high purity, dry bromine and substantially bromine-free water, and does not require additional environmental treatment of by-products.

SUMMARY OF THE INVENTION

To achieve the foregoing and other objects, and in accordance with the purposes of the present invention, as embodied and broadly described herein, one characterization of the present invention is a process comprising fractionating a wet bromine liquid in a first fractionator at conditions to produce at least a substantially dry bromine liquid and water saturated with bromine. The water saturated with bromine is fractionated in a second fractionator at conditions to produce at least substantially bromine-free water.

In another characterization of the present invention, a process is provided which comprises contacting wet bromine liquid with substantially dry bromine vapor so as to volatilize substantially all water dissolved in the wet bromine liquid and produce a substantially dry bromine liquid and a first bromine and water vapor. The first bromine and water vapor are condensed to form at least a first liquid phase comprising bromine saturated with water and a second liquid phase comprising water saturated with bromine. The first liquid phase and the second liquid phase are separated and the second liquid phase is contacted with substantially pure water vapor so as to volatilize substantially all bromine dissolved in the water and produce substantially bromine-free liquid water and a second bromine and water vapor.

In still another characterization of the present invention, a system is provided for drying wet bromine liquid which comprises a first fractionator, a heat exchanger, a separator and a second fractionator. The first fractionator has an inlet in the upper end thereof for wet bromine liquid, an outlet in the lower end thereof for substantially dry bromine liquid and an outlet in the upper end thereof for a first bromine and water vapor. The first fractionator is configured to countercurrently contact wet bromine liquid with substantially dry bromine vapor so as to volatilize substantially all water dissolved in the wet bromine liquid and produce a substantially dry bromine liquid. The heat exchanger is in fluid communication with the upper outlet of the first fractionator for condensing the first bromine and water vapor to form at least a first liquid phase comprising bromine saturated with water and a second liquid phase comprising water saturated with bromine. The separator is in fluid communication with the heat exchanger for separating the first liquid phase and the second liquid phase. The second fractionator is in fluid communication with the separator and has an inlet in the upper end thereof for the second liquid phase, an outlet in the lower end thereof for substantially bromine-free water and an outlet in the upper end thereof for a second water and bromine vapor. The second fractionator is configured to countercurrently contact the second liquid phase with substantially pure water vapor so as to volatilize substantially all bromine dissolved in the water and produce substantially bromine-free water

BRIEF DESCRIPTION OF THE DRAWINGS

The accompanying drawings, which are incorporated in and form a part of the specification, illustrate the embodiments of the present invention and, together with the description, serve to explain the principles of the invention.

In the drawings.

DETAILED DESCRIPTION OF THE PREFERRED EMBODIMENTS

Figure 2:
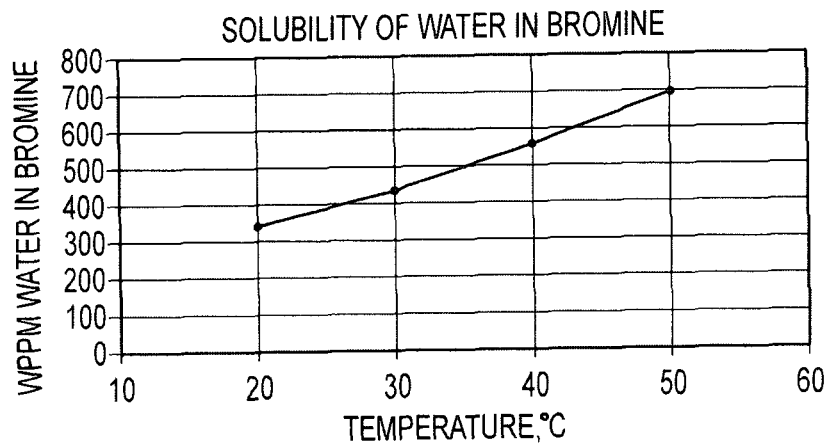
FIG. 2 is a graph illustrating the solubility of water in bromine.
Figure 3:
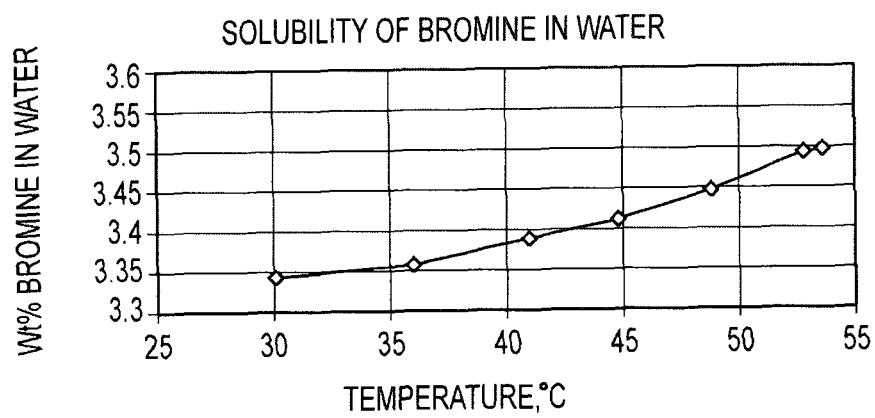
FIG. 3 is a graph illustrating the solubility of bromine in water.

The term "wet bromine liquid" as used herein refers to bromine liquid having water dissolved therein and may also include free water, especially where liquid bromine is separated by gravity from water. As illustrated in FIG. 2, water has limited solubility in liquid bromine which increases with temperature and at 50° C. is 700 wppm water in liquid bromine.

Suitable sources that may generate wet bromine liquid in various embodiments of the present invention include, but are not limited to, elemental bromine, bromine salts, aqueous hydrobromic acid, metal bromide salts, and the like. The bromine dried using the present invention may be a product stream for external sale in some embodiments or a recycle stream for internal reuse in other instances or a feed stream for downstream process in other examples. Certain embodiments of the methods of the invention are described below. Although figures are provided that schematically show certain aspects of the processes of the present invention, these figures should not be viewed as limiting on any particular process of the invention.

Figure 1:
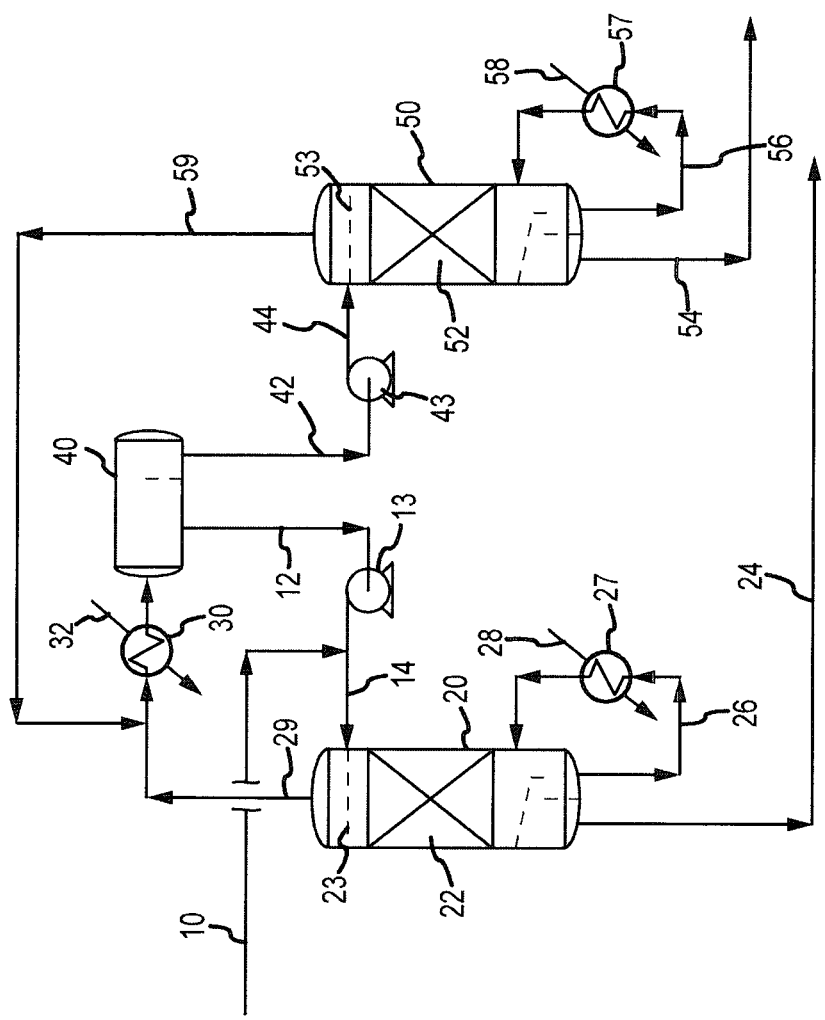
FIG. 1 is a schematic of one embodiment of the processes of the present invention.

A schematic generally depicting the processes and systems of the present invention is illustrated in FIG. 1 and depicts some aspects of certain embodiments of the processes of the present invention. In accordance with the schematic as illustrated in FIG. 1, a stream 10 of wet bromine liquid may be combined with a pumped recycle steam 12 of wet bromine liquid and introduced at a temperature of from about 40° C. to about 150° C. and a pressure of about 1.50 barg to about 10 barg into a bromine fractionator 20. Fractionator 20 may contain a number of trays or equivalent packing material, both identified as 22 in FIG. 1, as will be evident to a skilled artisan. The wet bromine liquid may be introduced into bromine fractionator 20 above the top tray or the top of the packing material 22. Fractionator 20 may include a liquid distributor or manifold 23 to more uniformly distribute the wet bromine liquid throughout the internal, cross sectional area of bromine fractionator 20. A product stream 24 of substantially dry bromine liquid, for example containing less than about 5.0 wppm water, more preferably less about 1.0 wppm water, and most preferably less than about 0.5 wppm water, may be withdrawn at the bottom of fractionator 20 for further use, sale, or both. Another stream 26 of dry bromine liquid may be withdrawn from the bottom of the bromine fractionator 20 and vaporized in reboiler 27 by means of low pressure steam 28 in a manner as will be evident to a skilled artisan before being introduced back into fractionator 20 at or near the bottom thereof. In this manner, substantially dry bromine vapor may flow upwardly through fractionator 20 contacting the wet bromine liquid flowing downwardly through the fractionator. Given that water dissolved in the wet bromine liquid is the more volatile component, substantially all of the water dissolved in the wet bromine liquid may be volatilized and carried upwardly by bromine vapor which may be withdrawn from the top of bromine fractionator 20 via stream 29. The number of trays or volume of equivalent packing utilized in bromine fractionator 20 may be readily determined using an appropriate McCable Thiele diagram as will be evident to a skilled artisan.

The overhead vapor stream 29 may be condensed in a heat exchanger 30 against cooling water 32 and conveyed to a reflux separator drum 40 wherein the bromine and water may condense and separate into two liquid phases: bromine saturated with water and water saturated with bromine. Preferably, the reflux separator drum 40 is operated with a sufficiently long residence time to produce saturated liquid phases, i.e. bromine saturated with water and water saturated with bromine. The bromine saturated with water, i.e. wet bromine liquid, in stream 12 may be pumped, combined with stream 10 of wet bromine liquid feed to form stream 14, and introduced at or near the top of bromine fractionator 20 as previously described by any suitable means, such as pump 13. The water saturated with bromine in stream 42 may be pumped as stream 44 and introduced at or near the top of a water fractionator 50 by any suitable means, such as pump 43. Fractionator 50 may contain a number of trays or equivalent packing material, both identified as 52 in FIG. 1, as will be evident to a skilled artisan. The water saturated with bromine may be introduced into water fractionator 50 above the top tray or the top of the packing material 52. Fractionator 50 may include a liquid distributor or manifold 53 to more uniformly distribute the water saturated with bromine throughout the internal, cross sectional area of water 50. A product stream 54 of substantially bromine-free water, for example containing less than about 5.0 wppm bromine, more preferably less than about 1.0 wppm bromine, and most preferably less than about 0.5 wppm bromine, may be withdrawn at or near the bottom of fractionator 50 for further use, sale, or both. Another stream 56 of relatively pure water may be withdrawn from the bottom of the water fractionator 50 and vaporized in reboiler 57 by means of low pressure low pressure steam 58 in a manner as will be evident to a skilled artisan before being introduced back into fractionator 50 at or near the bottom thereof. In this manner, substantially pure water vapor may flow upwardly through fractionator 50 contacting the water saturated with bromine flowing downwardly through the fractionator. Given that bromine dissolved in the water saturated with bromine is the more volatile component, substantially all of the bromine dissolved in the water saturated with bromine may be volatilized and carried upwardly by water vapor which may be withdrawn from the top of water fractionator 50 via stream 59. Stream 59 may be combined with overhead vapor stream 29 from bromine fractionator 20 prior to conveyance to heat exchanger 30 and reflux separator drum 40 to separate water and bromine into two phases as previously described. The number of trays or volume of equivalent packing utilized in bromine fractionator 50 may be readily determined using an appropriate McCable Thiele diagram as will be evident to a skilled artisan. It is preferred that the process described above with respect to FIG. 1 be operated continuously.

Figure 1A:
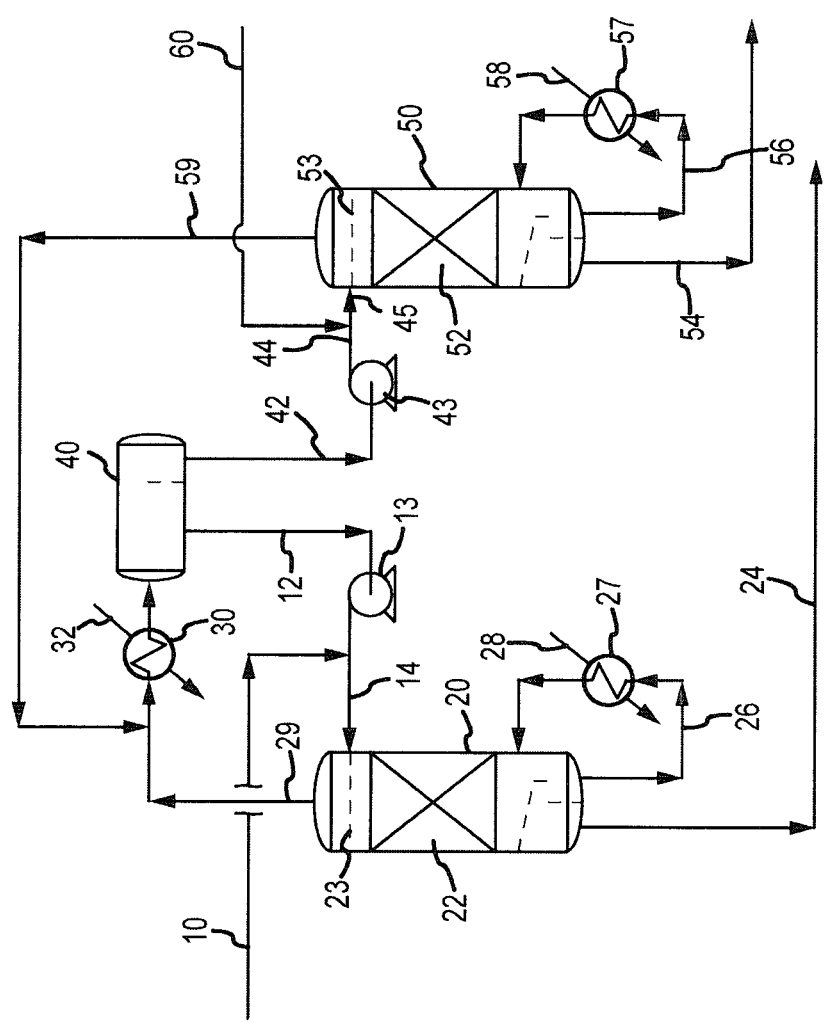
FIG. 1A is a schematic of another embodiment of the processes of the present invention.

In accordance with another embodiment of the processes and systems of the present invention schematically illustrated in FIG. 1A, a stream 60 of water containing bromine may be combined with the water saturated with bromine in stream 44 and introduced at or near the top of a water fractionator 50 by any suitable means, such as pump 43. Stream 60 may be from any suitable source and, where the process depicted in FIG. 1A is incorporated into another process, for example as depicted in and described below with respect to FIG. 4, stream 60 may be from the same process into which the process of the present invention is incorporated, a different process or source or a combination thereof.

Figure 4:
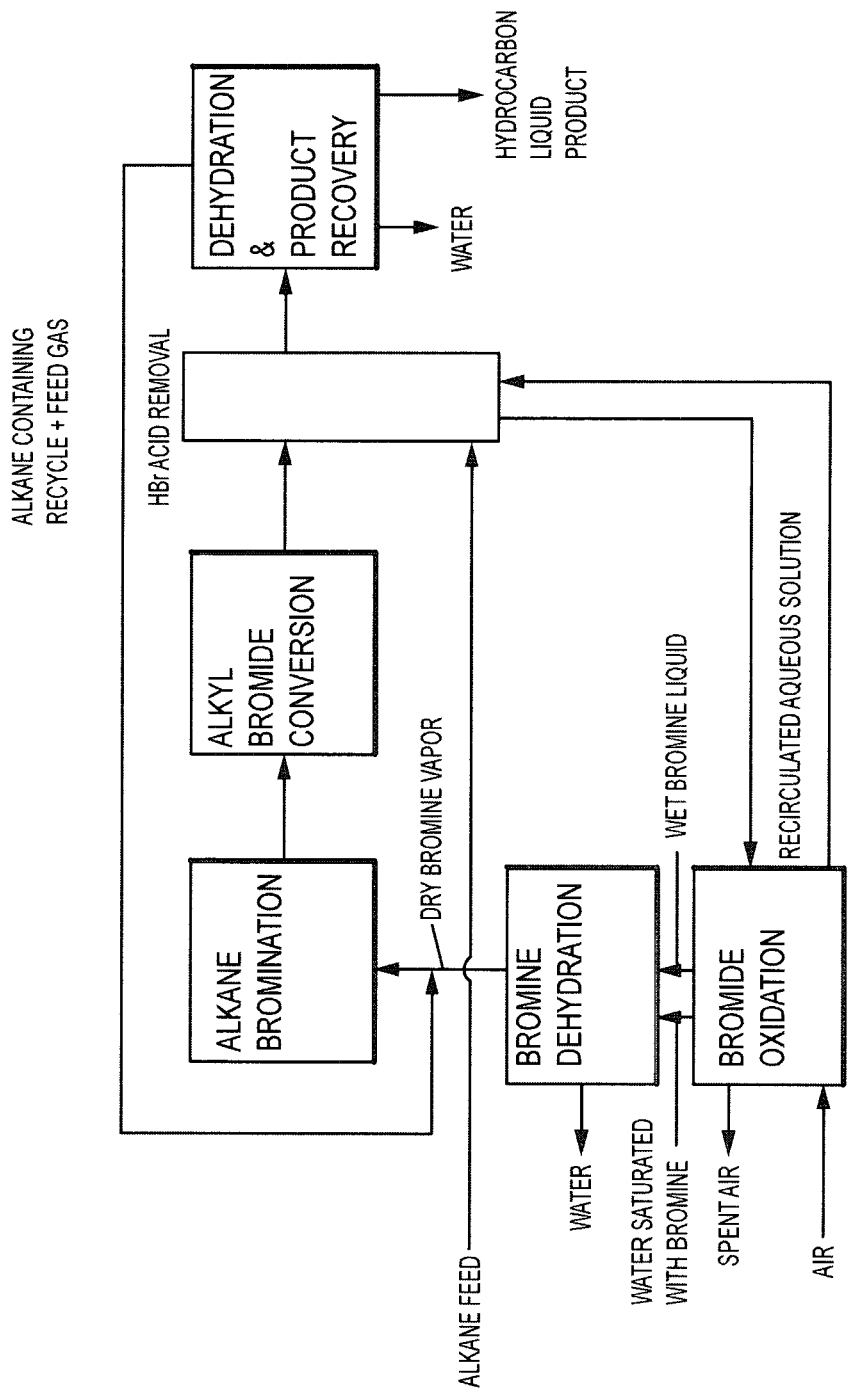
FIG. 4 is a block flow diagram of a still further embodiment of the processes of the present invention as incorporated into processes for the production of higher hydrocarbons from alkyl bromides.

A block flow diagram generally depicting an embodiment of the processes of the present invention as incorporated into a process for producing high molecular weight hydrocarbons is illustrated in FIG. 4. As utilized in this context, the term "high molecular weight hydrocarbons" as used herein refers to hydrocarbons comprising $C_3$ chains and longer hydrocarbon chains. In some embodiments, the higher molecular weight hydrocarbons may be used directly as a product (e.g., LPG, motor fuel, etc.). In other instances, the higher molecular weight hydrocarbon stream may be used as an intermediate product or as a feedstock for further processing. In other instances, the higher molecular weight hydrocarbons may be further processed, for example, to produce gasoline grade fuels, diesel grade fuels, and fuel additives. In some embodiments, the higher molecular weight hydrocarbons obtained by the processes of the present invention can be used directly as a motor gasoline fuel having a substantial aromatic content, as a fuel blending stock, or as feedstock for further processing, such as an aromatic feed to a process producing aromatic polymers, such as polystyrene or related polymers, or as an olefin feed to a process for producing polyolefins. The term "olefins" as used herein refers to hydrocarbons that contain two to six carbon atoms and at least one carbon-carbon double bond. The olefins may be further processed if desired. For instance, in some instances, the olefins produced by the processes of the present invention may be further reacted in a polymerization reaction (for example, a reaction using a metallocene catalyst) to produce poly(olefins), which may be useful in many end products such as plastics or synthetic lubricants.

The end use of the high molecular weight hydrocarbons, the olefins or mixtures thereof may depend on the particular catalyst employed in the oligomerization portion of the methods discussed below, as well as the operating parameters employed in the process. Other uses will be evident to those skilled in the art with the benefit of this disclosure.

In some embodiments, the present invention as depicted in FIG. 4 comprises reacting a feed gas stream with bromine from a suitable bromine source as previously discussed to produce alkyl bromides. As used herein, the term "alkyl bromides" refers to mono, di, and tri-brominated alkanes, and combinations of these. These alkyl bromides may then be reacted over suitable catalysts so as to form olefins, higher molecular weight hydrocarbons or mixtures thereof.

Lower molecular weight alkanes may be used as a feed stock for the methods described herein. A suitable source of lower molecular weight alkanes may be natural gas. As utilized throughout this description, the term "lower molecular weight alkanes" refers to methane, ethane, propane, butane, pentane or mixtures of two or more of these individual alkanes. The lower molecular weight alkanes may be from any suitable source, for example, any source of gas that provides lower molecular weight alkanes, whether naturally occurring or synthetically produced. Examples of sources of lower molecular weight alkanes for use in the processes of the present invention include, but are not limited to, natural gas, coal-bed methane, regasified liquefied natural gas, gas derived from gas hydrates and/or clathrates, gas derived from anaerobic decomposition of organic matter or biomass, gas derived in the processing of tar sands, and synthetically produced natural gas or alkanes. Combinations of these may be suitable as well in some embodiments. In some embodiments, it may be desirable to treat the feed gas to remove undesirable compounds, such as sulfur compounds and carbon dioxide. In any event, it is important to note that small amounts of carbon dioxide, e.g., less than about 2 mol %, can be tolerated in the feed gas to the processes of the present invention.

Although major aspects of what is believed to be the primary chemical reactions involved in the methods are discussed as it is believed that they occur, it should be understood that side reactions may take place. One should not assume that the failure to discuss any particular side reaction herein means that that reaction does not occur. Conversely, those that are discussed should not be considered exhaustive or limiting. Additionally, although figures are provided that schematically show certain aspects of the methods of the present invention, these figures should not be viewed as limiting on any particular method of the invention.

In accordance with the general depiction of the processes of the present invention as illustrated in FIG. 4, a gas stream containing lower molecular weight alkanes, comprised of a mixture of a feed gas plus a recycled gas stream, and a substantially dry bromine vapor are reacted in an alkyl bromination stage to produce alkyl bromides and hydrobromic acid. The resultant alkyl bromides are reacted over a suitable catalyst in the presence of hydrobromic acid in an alkyl bromide conversion stage to form olefins, higher molecular weight hydrocarbons or mixtures thereof. The particular olefins and higher molecular weight hydrocarbons produced will be dependent upon the catalyst employed in the alkyl bromide conversion stage, the composition of the alkyl bromides introduced into this stage and the exact operating parameters employed in this stage. The mixture of hydrobromic acid and olefins, higher molecular weight hydrocarbons or mixtures thereof are contacted with an aqueous solution in a hydrobromic acid (HBr) removal stage to remove hydrobromic acid from the olefins and higher molecular weight hydrocarbons. The resultant aqueous solution having hydrobromic acid dissolved therein may also be contacted with a feed gas in this HBr removal stage to remove any residual hydrocarbons from the aqueous solution.

The feed gas, residual hydrocarbons and olefins, higher molecular weight hydrocarbons or mixtures thereof are conveyed to a dehydration and product recovery unit wherein water may be removed from the remaining constituents. The feed gas and primarily methane and ethane hydrocarbons are then separated from the olefins, higher molecular weight hydrocarbons or mixtures thereof and conveyed to the alkane bromination stage of the present invention. The remaining olefins, higher molecular weight hydrocarbons or mixtures thereof are removed from the dehydration and product recovery stage for use as a fuel, a fuel blend or for further petrochemical or fuel processing.

As further generally illustrated in FIG. 4, the aqueous solution containing hydrobromic acid may be conveyed to a bromide oxidation stage. The aqueous solution that is used to contact the olefins, higher molecular weight hydrocarbons or mixtures thereof may contain a partially oxidized metal bromide salt or the aqueous solution may be passed through a bed of a partially oxidized metal bromide salt in the bromide oxidation stage of the process. Hydrobromic acid that is dissolved in the aqueous solution may be neutralized by the partially oxidized metal bromide salt to yield a metal bromide salt and water. The resultant metal bromide salt may, be oxidized with air in the bromide oxidation stage of the present invention to yield bromine vapor entrained with spent air and moisture which are subsequently cooled, via suitable means such as against cooling water in heat exchangers, to condense out bromine and water from spent air into two immiscible liquid streams: wet liquid bromine and water saturated with bromine. The same stage also yields a partially oxidized metal bromide salt which may be reused to neutralize and remove hydrobromic acid from the aqueous solution used to contact the olefins, higher molecular weight hydrocarbons or mixtures thereof produced by the process.

The wet liquid bromine stream and the water saturated with bromine stream may be conveyed to the bromine dehydration stage of the present invention which comprises two stage fractionation system as previously described in detail above with respect to FIG. 1A to generate a substantially dry bromine liquid, for example containing less than 1.0 wppm water, which may be pumped, vaporized and recycled to the alkane bromination stage. Elimination of substantially all water vapor from the bromination step by using substantially dry bromine eliminates the formation of unwanted carbon dioxide thereby increasing the selectivity of alkane bromination to alkyl bromides and eliminating the large amount of waste heat generated in the formation of carbon dioxide from alkanes. A substantially pure water phase, for example containing less than about 1.0 wppm bromine, may also be removed from the stage for further use, sale or both.

To facilitate a better understanding of the present invention, the following examples of certain aspects of some embodiments are given. The following examples should not be read or construed in any manner to limit, or define, the entire scope of the invention.

Example 1

A stream of wet bromine liquid at 105° C. and 10 barg and containing 1,500 wppm water is fed at a rate of 1,000 kg/h into the top of a bromine fractionator, having a packed bed with total packing height of 14 meter. A thermosyphon reboiler operates with a boilup ratio of 0.11, a return stream vapor fraction of 0.25 and a duty of 5.55 kW. A water bromine vapor mixture flows upwardly through the fractionator contacting wet bromine liquid flowing downwardly through the fractionator over the packed bed. Vapor leaving the top of the bromine fractionator is condensed in a suitable heat exchanger, and the water bromine phases are separated in reflux separator drum into two liquid phases: water rich phase and bromine rich phase. The bromine rich phase (153 kg/h, at 59° C. and 1,693 wppm water) is returned to the bromine fractionator as reflux by mixing with the feed stream. The bottoms bromine product (998 kg/h) contains <1.0 wppm water.

The water rich phase from the reflux separator drum (1.6 kg/h and 3.7 wt % $Br_2$) is routed to the top of the water fractionator, where the bromine is stripped off to yield a bottoms water product with <1.0 wppm bromine (1.5 kg/h). The water fractionator consists of a 4 meter high packed bed. The thermosyphon reboiler in this fractionator operates with a boilup ratio of 0.125, return stream vapor fraction of 0.2, and a duty of 0.12 kW. The water bromine vapor mixture leaving the top of the water fractionator is combined with the vapor leaving the top of the bromine fractionator prior to being condensed in a suitable heat exchanger and conveyed to the reflux separator drum for separation of the water and bromine liquid phases. The condenser duty is 9.2 kW. Operation data are summarized in the following Table 1.

TABLE 1

|  | Bromine Fractionator | Water Fractionator |
| --- | --- | --- |
| Feed Stage | Top of tower | Top of tower |
| Feed Rate, kg/h [Note 1] | 1,153 | 1.6 |
| Feed Composition [Note 2] |  |  |
| Bromine, wt % | 99.85 | 3.71 |
| Water, wt % | 0.15 | 96.29 |
| Packing Height (m) | 14 | 4 |
| Reboiler Duty, kW | 5.55 | 0.12 |
| Reboiler Temperature, ° C. | 81 | 120 |
| Reboiler Pressure, barg | 1.0 | 1.0 |
| Shared Condenser Duty, kW | 9.2 | |
| Shared Condenser Temperature, ° C. | 53 | |
| Shared Condenser Pressure, barg | 0.7 | |

[Note 1]:
Feed rate herein refers to the flow rate of the liquid stream entering the top of tower.
[Note 2]:
Feed composition herein refers to the composition of the liquid stream entering the top of tower.

Example 2

A stream of wet bromine liquid at 50° C. and 1.2 barg and having 1,000 wppm water is fed at a rate of 1,000 kg/h into the top of a bromine fractionator, having a packed bed with total packing height of 14 meter. A thermosyphon reboiler operates a duty of 7.07 kW. A water bromine vapor mixture flows upwardly through the fractionator contacting wet bromine liquid flowing downwardly through the fractionator over the packed bed. Vapor leaving the top of the bromine fractionator is condensed in a suitable heat exchanger, and the water bromine phases are separated in reflux separator drum into two liquid phases: water rich phase and bromine rich phase. The bromine rich phase (51 kg/h, at 59° C.) is returned to the bromine fractionator as reflux by mixing with the feed stream. The bottoms bromine product contains <1.0 wppm water.

A stream of water containing 4 wt % bromine (117 kg/h, at 50° C. 1.2 barg) combines the water rich phase from the reflux separator drum (1.7 kg/h and 3.7 wt % $Br_2$) and the mixture is routed to the top of the water fractionator, where the bromine is stripped off to yield a bottoms water product with <1.0 wppm bromine (113 kg/h). The water fractionator consists of a 4 meter high packed bed. The thermosyphon reboiler in this fractionator operates with a duty of 9.88 kW. The water bromine vapor mixture leaving the top of the water fractionator is combined with the vapor leaving the top of the bromine fractionator prior to being condensed in a suitable heat exchanger and conveyed to the reflux separator drum for separation of the water and bromine liquid phases. The condenser duty is 3.8 kW. Operation data are summarized in the following Table 2.

TABLE 2

|  | Bromine Fractionator | Water Fractionator |
| --- | --- | --- |
| Feed Stage | Top of tower | Top of tower |
| Feed Rate, kg/h [Note 1] | 1,051 | 116 |
| Feed Composition [Note 2] |  |  |
| Bromine, wt % | 99.90 | 96.0 |
| Water, wt % | 0.10 | 0.04 |
| Packing Height (m) | 14 | 4 |
| Reboiler Duty, kW | 7.07 | 9.88 |
| Reboiler Temperature, ° C. | 81 | 120 |
| Reboiler Pressure, barg | 1.0 | 1.0 |

TABLE 2-continued

|  | Bromine Fractionator | Water Fractionator |
|---|---|---|
| Shared Condenser Duty, kW |  | 3.8 |
| Shared Condenser Temperature, ° C. |  | 53 |
| Shared Condenser Pressure, barg |  | 0.7 |

[Note 1]:
Feed rate herein refers to the flow rate of the liquid stream entering the top of tower.
[Note 2]:
Feed composition herein refers to the composition of the liquid stream entering the top of tower.

The processes and systems of the present invention are less expensive than conventional processes since the substantially dry bromine vapor that may be produced by the process of the present invention permits the use of less expensive alloys, for example Hastelloy or Inconel for reboiler 27 and carbon steel for reboiler 57 than those that have been previously used, for example tantalum for reboiler 27 and titanium for reboiler 57, to counteract the highly corrosive natures of wet bromine liquid and bromine-containing water. Further, since the processes and systems of the present invention operate at low pressures in the range of about 1.5 barg to about 10 barg and at relatively low temperatures in the range of about 40° C. to about 150° C., such operating conditions permit the use of less expensive equipment of relatively simple design that are constructed from readily available metal alloys or polymer-lined or glass-lined vessels, piping and pumps.

While the processes and systems of the present invention have been described above with respect to drying bromine, i.e. removing water from bromine, it will be understood by a skilled artisan that the processes and systems of the present invention may also remove other impurities, such as chlorine and dissolved light gas components such as nitrogen and methane, which may require certain alterations to the operating parameters of the processes and systems.

While the foregoing preferred embodiments of the invention have been described and shown, it is understood that the alternatives and modifications, such as those suggested and others, may be made thereto and fall within the scope of the invention.

We claim:

1. A process comprising:
   fractionating a wet bromine liquid in a first fractionator at conditions to produce at least a substantially dry bromine liquid and a first stream of bromine vapor and water vapor;
   condensing the first stream of bromine vapor and water vapor to form at least a first liquid phase comprising bromine saturated with water and a second liquid phase comprising water saturated with bromine;
   separating the first liquid phase and the second liquid phase;
   fractionating said second liquid phase in a second fractionator at conditions to produce at least substantially bromine-free water and a second stream of bromine vapor and water vapor; and
   combining the second stream of bromine vapor and water vapor generated in the second fractionator with the first stream of bromine vapor and water vapor generated in the first fractionator prior to the step of condensing.

2. The process of claim 1 wherein said substantially dry bromine liquid contains less than about 5.0 wppm water.

3. The process of claim 2 wherein said substantially dry bromine liquid contains less than about 1.0 wppm water.

4. The process of claim 3 wherein said substantially dry bromine liquid contains less than about 0.5 wppm water.

5. The process of claim 1 wherein the temperature at which such first fractionator operates is from about 40° C. to about 150° C.

6. The process of claim 1 wherein the pressure at which such first fractionator operates is from about 1.50 barg to about 10 barg.

7. The process of claim 1 wherein said substantially bromine-free water contains less than about 5.0 wppm bromine.

8. The process of claim 7 wherein said substantially bromine-free water contains less than about 1.0 wppm bromine.

9. The process of claim 8 wherein said substantially bromine-free water contains less than about 0.5 wppm bromine.

10. The process of claim 1 wherein the temperature at which such second fractionator operates is from about 100° C. to about 120° C.

11. The process of claim 1 wherein the pressure at which such second fractionator operates is from about 0.7 barg to about 1.0 barg.

12. A process comprising:
   fractionating a wet bromine liquid in a first fractionator at conditions to produce at least a substantially dry bromine liquid and a first stream of bromine vapor and water vapor, the wet bromine liquid being contacted with substantially dry bromine vapor in said first fractionator so as to volatilize substantially all water dissolved in the wet bromine liquid;
   condensing the first stream of bromine vapor and water vapor to form at least a first liquid phase comprising bromine saturated with water and a second liquid phase comprising water saturated with bromine;
   separating the first liquid phase and the second liquid phase; and
   fractionating said second liquid phase in a second fractionator at conditions to produce at least substantially bromine-free water and a second stream of bromine vapor and water vapor.

13. The process of claim 12 further comprising:
   heating a portion of the substantially dry bromine liquid to form at least a portion of the substantially dry bromine vapor used to contact wet bromine liquid in the first fractionator.

14. The process of claim 12 wherein said step of contacting is performed countercurrently.

15. A process comprising:
   fractionating a wet bromine liquid in a first fractionator at conditions to produce at least a substantially dry bromine liquid and a first stream of bromine vapor and water vapor;
   condensing the first stream of bromine vapor and water vapor to form at least a first liquid phase comprising bromine saturated with water and a second liquid phase comprising water saturated with bromine;
   separating the first liquid phase and the second liquid phase; and
   fractionating said second liquid phase in a second fractionator at conditions to produce at least substantially bromine-free water and a second stream of bromine vapor and water vapor, the water saturated with bromine being contacted with substantially pure water vapor in the second fractionator so as to volatilize substantially all bromine dissolved in the water.

16. The process of claim 15 further comprising:
heating a portion of the substantially bromine-free water to form at least a portion of the substantially pure water vapor used to contact the water saturated with bromine in the second fractionator.

\* \* \* \* \*